United States Patent
Lee et al.

(10) Patent No.: US 6,476,076 B1
(45) Date of Patent: Nov. 5, 2002

(54) VANILLOID ANALOGUES CONTAINING RESINFERATOXIN PHARMACOPHORES AS POTENT VANILLOID RECEPTOR AGONISTS AND ANALGESICS, COMPOSITIONS AND USES THEREOF

(75) Inventors: Jeewoo Lee, Seoul (KR); Uhtaek Oh, Seoul (KR); Young-Ho Park, Seoul (KR); Young-Ger Suh, Seoul (KR); Hyeung-Geun Park, Seoul (KR); Hee-Doo Kim, Seoul (KR)

(73) Assignees: Pacific Corporation (KR); Digital Biotech Co., Ltd. (KR)

( * ) Notice: Subject to any disclaimer, the term of this patent is extended or adjusted under 35 U.S.C. 154(b) by 0 days.

(21) Appl. No.: 09/914,000

(22) PCT Filed: Feb. 21, 2000

(86) PCT No.: PCT/KR00/00137

§ 371 (c)(1),
(2), (4) Date: Aug. 20, 2001

(87) PCT Pub. No.: WO00/50387

PCT Pub. Date: Aug. 31, 2000

(30) Foreign Application Priority Data

Feb. 22, 1999 (KR) .............................. 99-5751

(51) Int. Cl.$^7$ ................... A01N 47/28; A01N 37/18; A61K 31/17; A61K 31/16; C07C 69/00
(52) U.S. Cl. ................. 514/580; 514/588; 514/599; 514/613; 514/718; 560/8; 560/142
(58) Field of Search ............... 560/8, 107, 110, 560/129, 142; 564/17, 47, 161, 182, 201, 202; 514/580, 588, 599, 534, 718, 613

(56) References Cited

U.S. PATENT DOCUMENTS 5,431,914 A * 7/1995 Adekunle et al. .......... 424/401

OTHER PUBLICATIONS

Analogues of Capsaicin with Agonist Activity as Novel Analgesic Agents; Structure–Activity Studies. 2. The amide Bond "B–Region" Walpole et al, J. Med. Chem. vol. 36 pp 2373–2380 (1993).*

Analogues of Capsaicin with Agonist Activity as Novel Analgesic Agents; Structure–Activity Studies. 3. The Hydrophobic Side–Chain "C–Region" Walpole et al, J. Med. Chem. vol. 36 pp 2381–2389 (1993).*

"Analogues of Capsaicin with Agonist Activity as Novel Analgesic Agents; Structure–Activity Studies. 4. Potent, Orally Active Analgesics" Wriggleworth et al, J. Med. Chem. vol. 39 pp 4942–4951 (1996).*

"3–Acyloxy–2–phenylalkylpropyl Amides and Esters of Homovanillic Acid as Novel Vanilloid Receptor Agonists" Lee et al, Biorganic and Medicinal Chemistry Letters vol. 9 pp 2909–2914 (1999).*

* cited by examiner

Primary Examiner—Mukund J. Shah
Assistant Examiner—Zachary Tucker
(74) Attorney, Agent, or Firm—Anderson Kill & Olick, PC

(57) ABSTRACT

The present invention is related to new vanilloid analogues containing resiniferatoxin pharmacophores, pharmaceutical compositions comprising such analogues, and their uses as vanilloid receptor agonists and potent analgesics. The present invention provides a pharmaceutical composition for treating acute, chronic, inflammatory or neuropathic pains or for treating bladder hypersensitivity.

12 Claims, No Drawings

VANILLOID ANALOGUES CONTAINING RESINFERATOXIN PHARMACOPHORES AS POTENT VANILLOID RECEPTOR AGONISTS AND ANALGESICS, COMPOSITIONS AND USES THEREOF

CROSS REFERENCE TO RELATED APPLICATION

This application is a 371 of International Application PCT/KR00/00137, with an international filing date of Feb. 21, 2000, designating the United States of America.

BACKGROUND OF THE INVENTION

1. Technical Field of the Invention

The present invention relates to vanilloid analogues containing resiniferatoxin pharmacophores, pharmaceutical compositions comprising such analogues, and methods of using such analogues as vanilloid receptor agonists and potent analgesics.

2. Related Arts of the Invention

Capsaicin (CAP), which has the structure shown hereinafter, stimulates and then desensitizes sensory afferent C-fibers. The induced desensitization may have an application in arthritis, asthma, allergic responses including rhinitis, fever, pain, bladder hypersensitivity and the like.

Besides, the vanilloid receptor(VR)(or capsaicin receptor) is a specific neuronal membrane recognition site for CAP and related irritant compounds. It is expressed almost exclusively by primary sensory neurons involved in nociception and neurogenic inflammation. The receptor functions as a cation-selective ion channel with a preference for calcium, and its functional subtype, VR1, activated by both CAP and noxious heat has recently been cloned. Its desensitization caused by specific ligands has been recognized as a promising therapeutic approach to mitigate neuropathic pain and other pathological conditions in which neuropeptides released from primary sensory neurons play a crucial role.

Most exogenous VR agonists which are being developed or used as analgesics are structually related to CAP(i.e., Zostrix™, Olvanil™, SDZ-249482™, and DA-5018™) and resiniferatoxin. Their structures include a common vanilloid ring which appears to be important for agonist activity. However, in a recent report, it was demonstrated that compounds lacking the vanilloid moiety, such as sesquiterpenoid unsaturated dialdehydes or triprenyl phenol, may also activate the receptor. Although receptor antagonists are fewer, several compounds such a capsazepine, which acts competitively at the CAP binding site, the channel blocker ruthenium red and capsazocaine have been reported.

Resiniferatoxin (RTX), a tricyclic diterpene isolated from *Euphorbia resinifera*, has been regarded as an ultrapotent CAP analogue. Indeed, the specific binding of RTX to the CAP binding site in dorsal root ganglia has been demonstrated with labeled [$^3$H]RTX. RTX is being developed as an ultrapotent sensory neuron desensitizing agent for the treatment of urinary urge incontinence and the pain assoaciated with diabetic neuropathy. Recently, a totally enantiocontrolled synthesis and a conformational analysis of RTX have been reported. However, the pharmacophoric groups of RTX have not yet been clearly defined, although structure-activity studies suggest that the $C_{20}$-homovanillic moiety, the $C_3$-keto group, and the ortho-ester phenyl group on ring C are crucial structural elements responsible for the extremely high potency of RTX. The lower potency of CAP relative to RTX, on the other hand, may be rationalized by the lack of some of these critical pharmacophoric groups, especially $C_3$-keto group.

U.S. Pat. No. 4,939,149 discloses a method for desensitizing a subject animal by administering a therapeutically effective desensitizing amount of RTX for desensitizing the animal to neurogenic inflammation, to chemically and thermally induced pain and to responses involving sensory afferent pathways sensitive to CAP.

Although a number of vanilloid agonist based on the structures of CAP and RTX have been reported as potential analgesics (e.g., U.S. Pat. No. 5,021,450 discloses homovanillyl diterpene derivatives such as 12-deoxyphorbol 13-phenylacetate 20-homovanillate and mezerein 20-homovanillate as mimics of RTX), these CAP-like analogues are limited by their intrinsic lower potency and narrow therapeutic index. RTX, on the other hand, is of limited availability from natural sources and is difficult to obtain synthetically due to its structural complexity.

The present inventors have made extensive researches to discover novel analgesic agents based on the vanilloid receptor, which has simpler structure than RTX or known RTX- or CAP-like analogues. As results thereof, we found that the new compounds having modifications on $C_{20}$-homovanillic moiety, the $C_3$-carbonyl, and the ortho-ester phenyl moiety as essential groups for recognition and binding showed potent vanilloid agonist activity in terms of the receptor binding assay and the CAP-activated single channel assay.

SUMMARY OF THE INVENTION

Thus, the present invention provides novel compounds represented by the following formula (I):

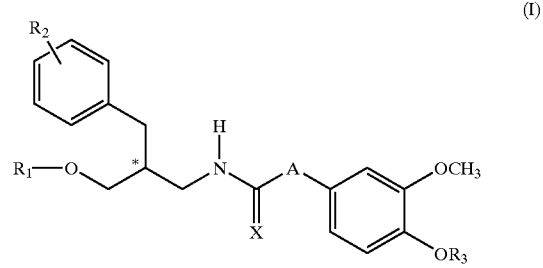

(I)

wherein,
- X is an oxygen or sulfuir atom;
- A is —NHCH$_2$— or —CH$_2$—;
- R$_1$ is a substituted or unsubstituted C$_{1-4}$alkylaryl group, or the group of formula: R$_4$CO— wherein R$_4$ is an alkyl group having 1 to 18 carbon atoms, an alkenyl group having 2 to 18 carbon atoms, or substituted or unsubstituted aryl group having 6 to 10 carbon atoms;
- R$_2$ is a hydrogen atom, an alkyl group having 1 to 6 carbon atoms, an alkoxy group having 1 to 6 carbon atoms, a haloalkyl group having 1 to 6 carbon atoms or a halogen atom;
- R$_3$ is a hydrogen atom, an alkyl group having 1 to 4 carbon atoms, an aminoalkyl, a diacid monoester or α-alkyl acid; and the asteric mark * indicates a chiral carbon atom, and their pharmaceutically acceptable salts.

The present invention also provides pharmaceutical compositions comprising the compound (I) as an active ingredient in an amount effective to alleviate pain, together with a pharmaceutically acceptable carrier.

The present invention also provides a use of the compounds as an active ingredient in medicines for treating pain or urinary incontinence.

The present invention still provides processes for preparing the compound (I).

DETAILED DESCRIPTION OF THE INVENTION

The compounds of the present invention is represented by the following formula (I):

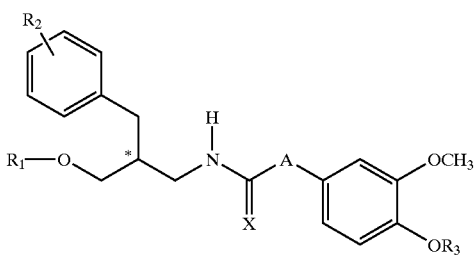

(I)

wherein,

X is an oxygen or sulfur atom;

A is —NH—CH$_2$— or —CH$_2$—;

R$_1$ is a substituted or unsubstituted C$_{1-4}$alkylaryl group, or the group of formula R$_4$CO— wherein R$_4$ is an alkyl group having 1 to 18 carbon atoms, an alkenyl group having 2 to 18 carbon atoms, or substituted or unsubstituted aryl group having 6 to 10 carbon atoms;

R$_2$ is a hydrogen atom, an alkyl group having 1 to 6 carbon atoms, an alkoxy group having 1 to 6 carbon atoms, a haloalkyl group having 1 to 6 carbon atoms or a halogen atom;

R$_3$ is an aminoalkyl, a diacid monoester or α-alkyl acid; and the asteric mark * indicates a chiral carbon atom, and their pharmaceutically acceptable salts.

The preferred compounds may be represented by the following formula (I-a) and (I-b):

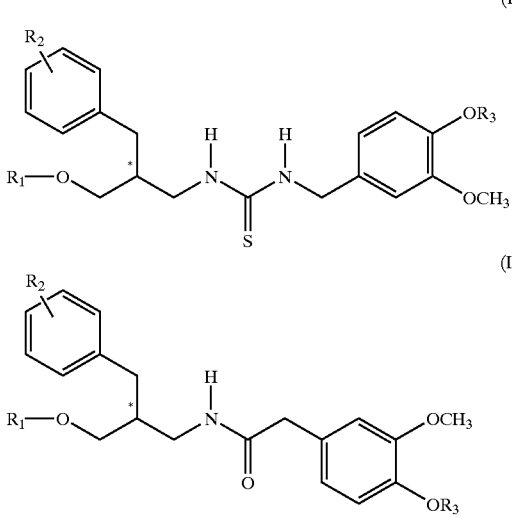

wherein, R$_1$, R$_2$ and R$_3$ have the same meanings as defined above.

In a preferred embodiment, the compounds have the general formula (I-a) or (I-b) wherein R$_1$ is the group of formula R$_4$CO— wherein R$_4$ is an alkyl group having 1 to 18 carbon atoms; R$_2$ is an alkyl group having 1 to 6 carbon atoms; and R$_3$ is —(CH$_2$)$_n$NH$_2$, —CO(—CH$_2$)$_n$COOH or —(CH$_2$)$_n$COOH, wherein n is an integer of 1 to 4. When R$_1$ or R$_4$ is a substituted aryl group, the substituents may be one or more lower alkyls having 1 to 4 carbon atoms or halogen atoms.

In a more preferred embodiment, the compounds have the general formula (I-a) or (I-b) wherein R$_1$ is the group of formula R$_4$CO— wherein R$_4$ is an alkyl group having 1 to 6 carbon atoms; R$_2$ is an alkyl group having 1 to 6 carbon atoms; and R$_3$ is —CH$_2$CH$_2$NH$_2$, —COCH$_2$CH$_2$COOH or —CH$_2$COOH, In all cases, the compound (I) may be in racemic mixture, or in R or S stereoisomer. And, the present invention encompasses the compound (I) in the form of their pharmaceutically acceptable salts.

The compounds of the invention may be chemically synthesized by the methods in the reaction schemes hereinafter, which are merely exemplary and in no way limit the invention. The reaction schemes show the steps for preparing the representative compounds of the present invention, and other compounds also may be produced by following the steps with appropriate modifications of reagents and starting materials, which are envisaged by those skilled in the art.

GENERAL SYNTHETIC PROCEDURES

The syntheses of 3-acyloxy-2-benzylpropyl thiourea derivatives (7a–d) are outlined in Schemes 1 and 2. Monoalkylation of diethyl malonate with various benzyl halides, followed by LiAlH$_4$-reduction, produced the corresponding diols (2a–d). Monoacetylation of 2, conversion of the remaining alcohol function to an azide, and deprotection of the acetyl group afforded the intermediate 3-azido-2-benzyl-1-propanols (5a–d). Acylation of 5a–d with various acyl halides produced the corresponding esters 6a–d, which following the reduction of the azide group were condensed with 4-methoxymethyloxy-3-methoxybenzylisothiocyanate and hydrolyzed to the final desired products 7a–d. The alternative ether analogues, represented by the 3-benzyloxy-2-benzylpropyl thiourea derivatives, 9a,c, were synthesized from 5a,c as shown in Scheme 2. Two chiral analogues of 7a-I were synthesized from (R)-3-acetoxy-2-benzyl-1-propanol ((R)-3a) obtained from the enantioselective enzymatic acetylation of racemic 2-benzyl-1,3-propanediol (Scheme 3) following the same procedure for the synthesis of 7a-I.

The synthesis of O-acetic acid analogues (19a,b) of above thiourea derivatives is represented in scheme 4. 4-Hydroxy-3-methoxy-benzonitrile (11) was protected by MOM (methylmethylether) group to give 12, whose cyano group was reduced to amine by LiAlH$_4$ and then protected by CBZ (chlorobenzyl) group to 13. MOM group of 13 was deprotected and then the corresponding hydroxy group was alkylated by methyl bromoacetate to give 15. Methyl ester of 15 was hydrolyzed and then CBZ group was deprotected to give 17. Amine of 17 was condensed with isothiocyante 18a,b to give final desired products 19a,b, respectively.

The synthesis of O-succinic ester analogues (23a,b) of above thiourea derivatives is represented in scheme 5. Mono benzyl ester of succinic acid 20 was acylated with vanilloid 14 to give 21 whose benzyl groups are deprotected by hydrogenation to give 22. Amine of 22 was condensed with isothiocyanate 18a,b to give final desired products 23a,b, respectively.

The synthesis of O-aminoethyl analogues (28a,b) of amide derivatives is represented in scheme 6. Azido group of 24 was reduced to amine, which in situ was condensed with homovanillic pentafluoro ester to give 25. Hydroxy group of 25 was alkylated by dibromoethane to give 26 whose bromo group then was substituted by azido group to 27. Reduction of 27a,b afforded the final desired products 28a,b, respectively.

The synthesis of O-aminoethyl analogues (36a,b) of above thiourea derivatives is represented in scheme 7. Amine of 4-hydroxy-3-methoxybenzylamine 29 was protected by Boc group and then hydroxy was alkylated by dibromoethane to give 31. Bromo group of 31 was substituted by azido group and then N-Boc was deprotected to give 33. Amine of 33 was converted into the correspond isothiocyanate which was condensed with azide 6 to give thiourea 35. Azido group of 35a,b was reduced to afford final desired products 36a,b, respectively.

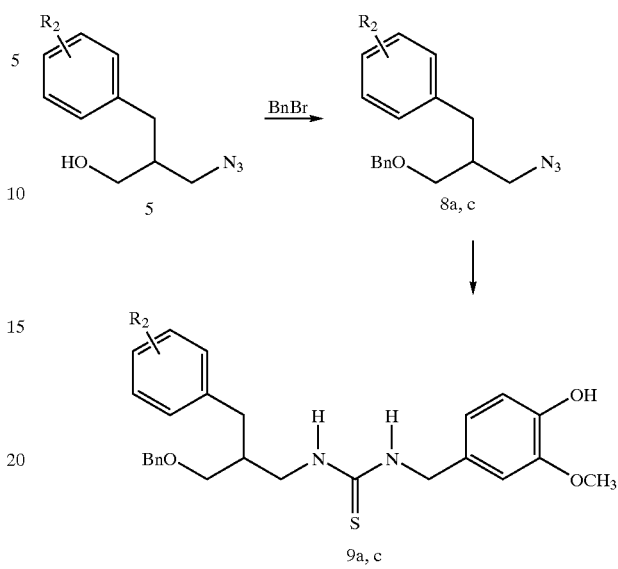

Scheme 2

(Bn : Benzyl)

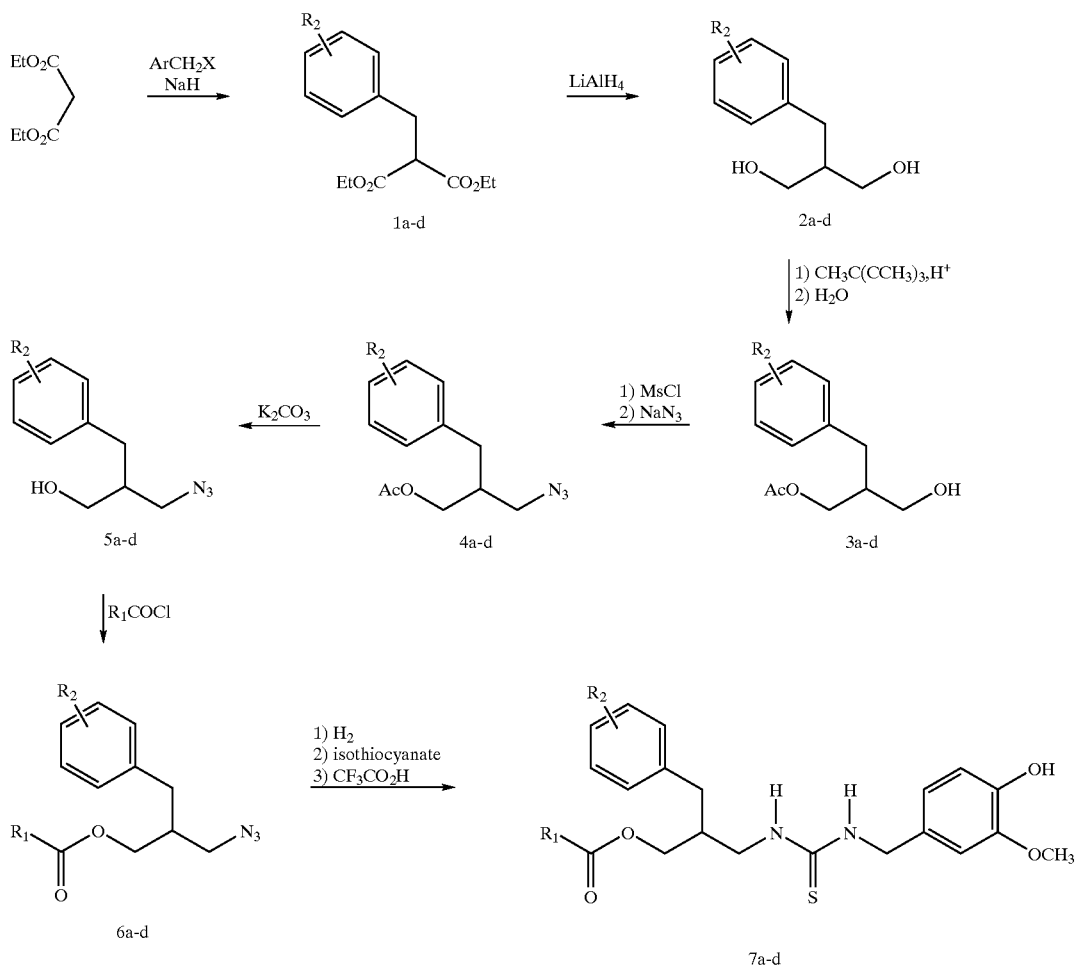

Scheme 1

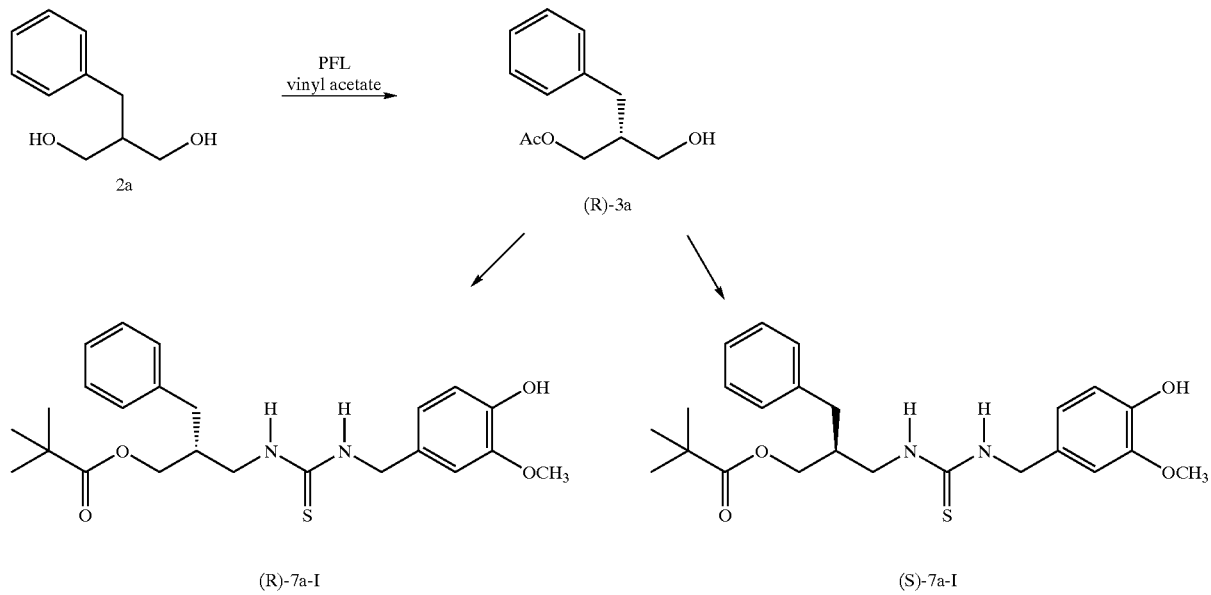
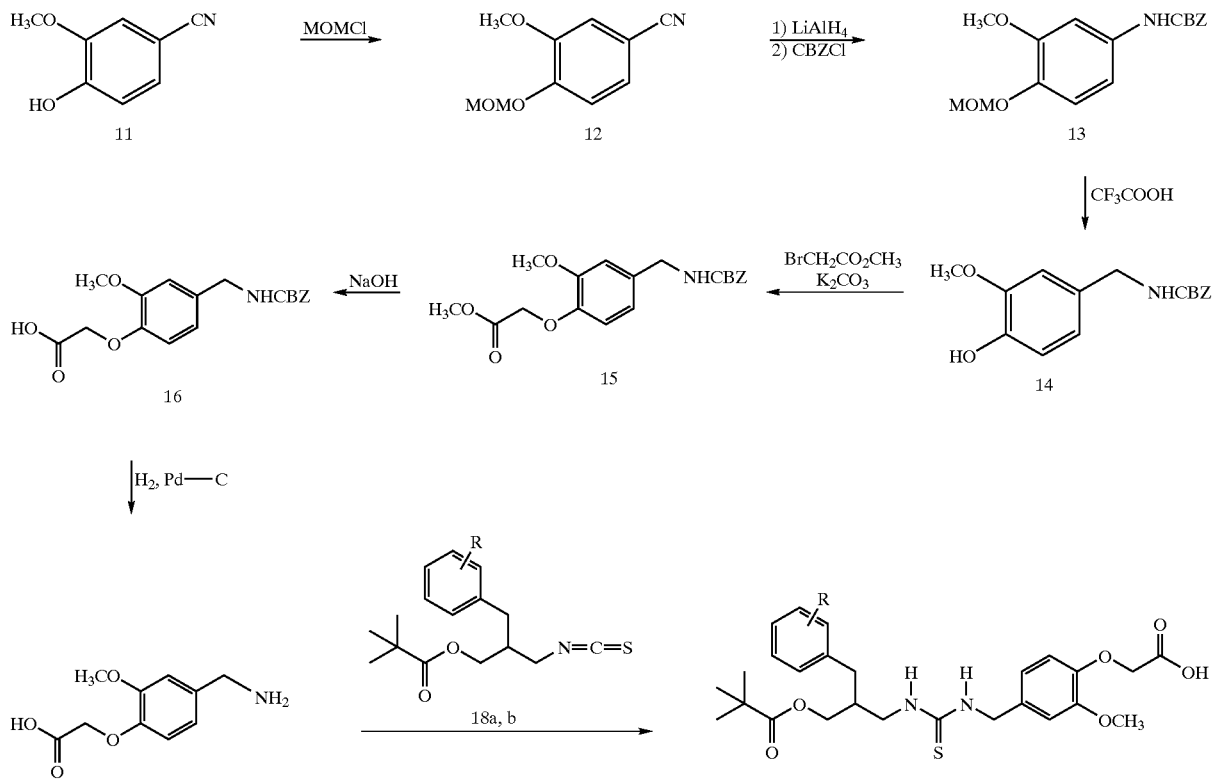
(MOMCl : Chloromethylmethylether
CBZCl : Benzylchloroformate)

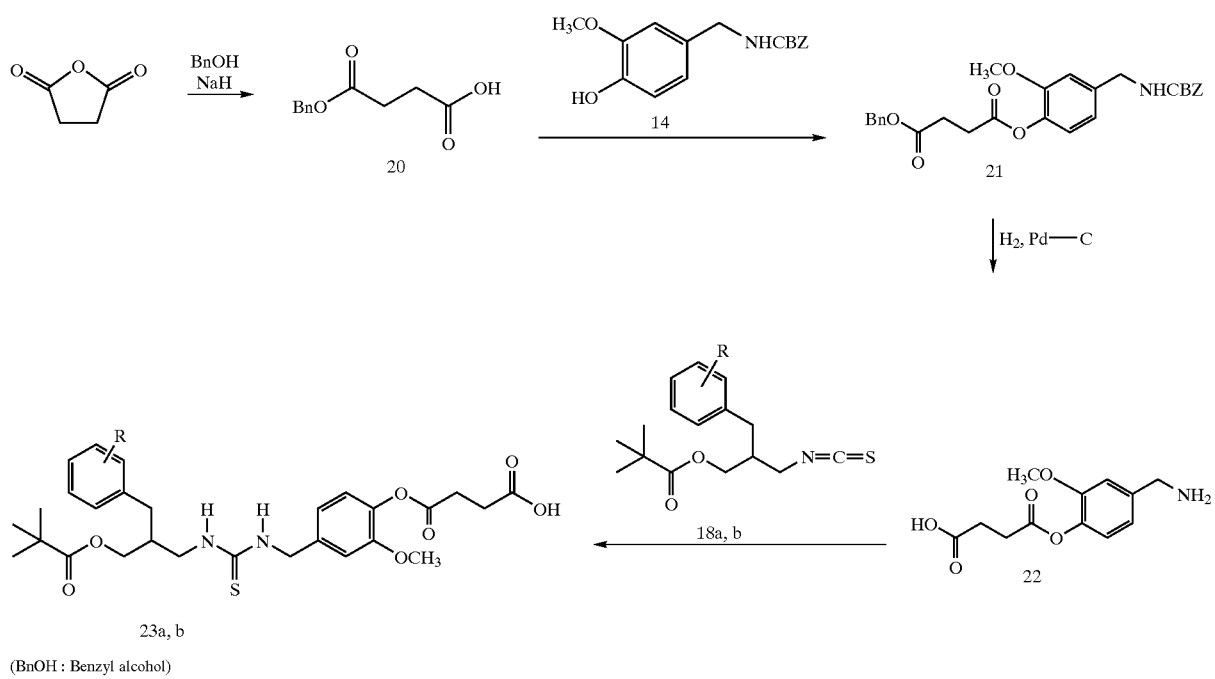
Scheme 5
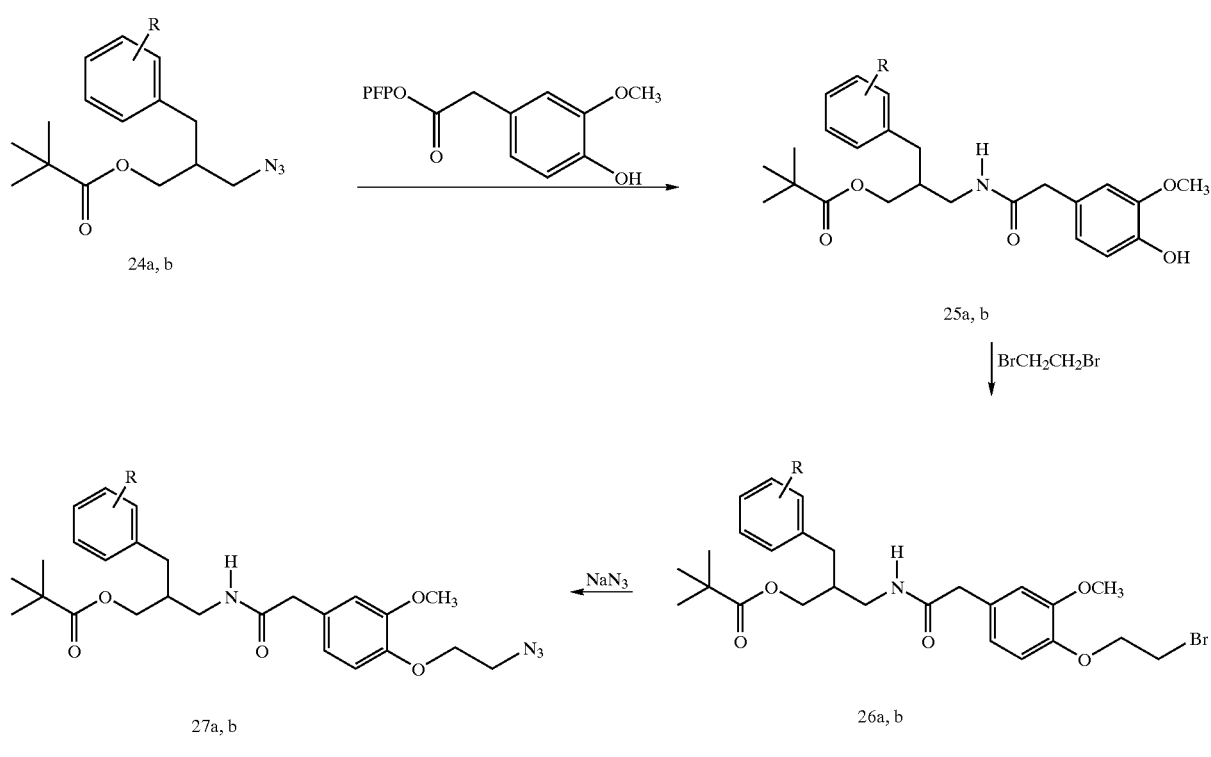
Scheme 6

-continued
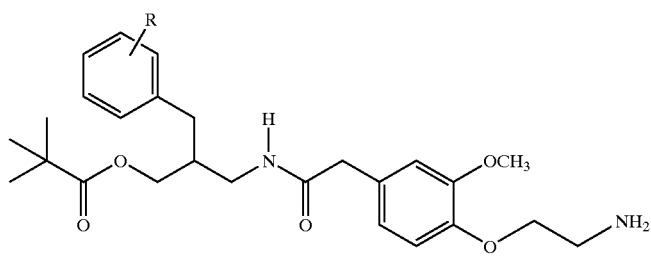
28a, b
(PFP: Pentafluorophenyl)
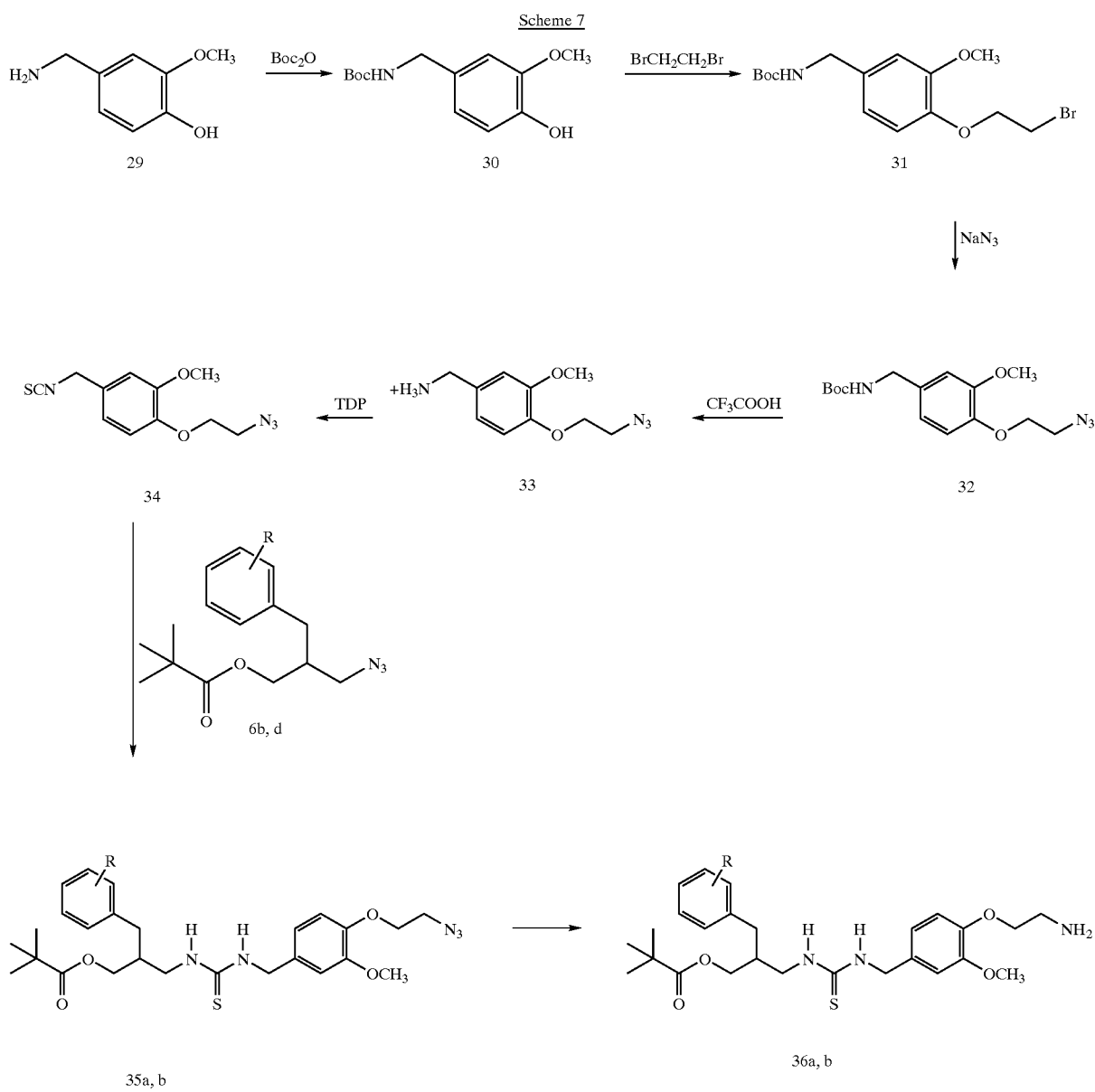
(Boc₂O : Di-t-butyl-di-carbonate
TDP : 1,1-Thiocarbonyl di-2(1H)-pyridone)

Structure of Capsaicin (CAP)

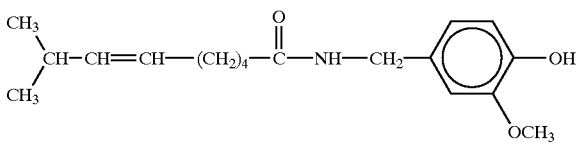

Structure of RTX

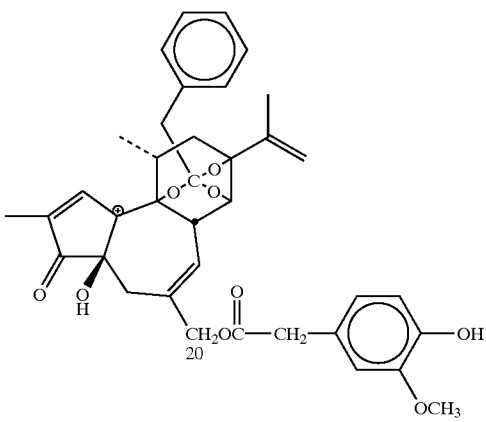

The compounds of the present invention can be made into pharmaceutical compositions by combination with appropriate medical carriers or diluents. For example, the compounds of the present invention can be dissolved in oils, propylene glycol or other solvents commonly used to prepare injectable solutions. Suitable carriers include, but not limited thereto, physiological saline, polyethylene glycol, ethanol, vegetable oils and isopropyl myristate. For topical application, the compounds of the invention can be formulated as an ointment or cream.

The pharmaceutical compositions comprising the compound of the present invention may be applied for the following occasions:
  to relieve pain caused by posttherpetic neuralgia, diabetic neuropathy, postrnastectomy pain syndrome, stump pain, reflex sympathetic dystrophy, trigeminal neuralgia, oral neuropathic pain, osteoarthritis, rheumatoid arthritis, fibromyalgia, Guillain-Barre syndrome, meralgia paraesthetica, burning mouth syndrome
  to ameliorate pain such as intractable pain due to bilateral peripheral neuropathy
  to relieve itch due to psoriasis, hemodyalisis, aquagenic pruritus, vulvar vestibulitis, notalgia paraesthetica, brachioradial prutitus, Lichen simplex chronicus
  to treat cluster headache, vasomotor rhinitis or perenial allergic rhinitis in the form of intranasal drop
  to treat bladder hypersensitivity or spinal detrusor hyper-reflexia in the form of intravesical solution.

The compound of the present invention has potent analgesic and antiinflammatory activity, and the pharmaceutical composition of the present invention thus may be employed to alleviate or relieve acute, chronic or inflammatory pains, suppress inflammation, or treat urge incontinence.

The following formulation methods and excipients are merely exemplary and in no way limit the invention.

The compounds of the present invention in pharmaceutical dosage forms may be used in the form of their pharmaceutically acceptable salts, and also may be used alone or in appropriate association, as well as in combination with other pharmaceutically active compounds.

The compounds of the present invention may be formulated into preparations for injections by dissolving, suspending, or emulsifying them in aqueous solvents such as normal saline, Dextrose 5%, or non-aqueous solvent such as vegetable oil, synthetic aliphatic acid glycerides, esters of higher aliphatic acids or propylene glycol. The formulation may include conventional additives such as solubilizers, isotonic agents, suspending agents, emulsifying agents, stabilizers and preservatives.

The desirable dose of the compounds of the present invention varies depending on the condition and weight of the subject, severity, drug form, route and period of administration, and may be chosen by those skilled in the art. However, in order to obtain desirable effects, it is generally recommended to administer 0.0001–100 mg/kg, preferably 0.001–100 mg/kg by weight/day of the compounds of the present invention. The dose may be administered in single or divided into several times per day. In terms of composition, the compounds should be present between 0.0001 to 10% by weight, preferably 0.0001 to 1% by weight based on the total weight of the composition. The pharmaceutical composition of the present invention can be administered to a subject animal such as mammals (rat, mouse, domestic animals or human) via various routes. All modes of administration are contemplated, for example, administration can be made orally, rectally or by intravenous, intramuscular, subcutaneous, intrathecal, epidural or intracerebroventricular injection.

EXAMPLES

General Procedure for the Synthesis of 1a–d

A cooled solution of diethylmalonate (6.4 g, 40 mmol) in DMF (20 mL) at 0° C. was treated with sodium hydride (60%, 1.92 g, 48 mmol) portionwise and stirred for 40 min at room temperature. The reaction mixture was treated with the corresponding substituted benzyl chlorides (48 mmol) and stirred overnight at room temperature. The mixture was diluted with $H_2O$ and extracted with EtOAc several times. The combined organic layer was washed with $H_2O$ and brine, dried over $MgSO_4$, and concentrated in vacuo. The residue was purified by flash column chromatography on silica gel with EtOAc/hexane (1:10) as eluant to give 1.

Example 1

Diethyl 3,4-Dimethylbenzylmalonate (1b)

70% yield, colorless oil; $^1$H NMR ($CDCl_3$) δ 6.9–7.05 (m, 3H), 4.14 (m, 4H, 2×$CO_2CH_2$), 3.61 (t, 1H, CH), 3.25 (d, 1H, $CH_2Ar$), 3.14 (d, 1H, $CH_2Ar$), 2.2–2.25 (m, 6H, 2×$CH_3$), 1.21 (m, 6H, 2×$CO_2CH_2C\underline{H}_3$).

Example 2

Diethyl 4-Chlorobenzylmalonate (1c)

74% yield, colorless oil; $^1$H NMR ($CDCl_3$) δ 7.25 (d, 2H), 7.16 (d, 2H), 4.14 (mn, 4H, 2×$CO_2CH_2$), 3.60 (t, 1H, CH), 3.18 (d, 2H, $CH_2Ar$), 1.21 (t, 6H, 2×$CO_2CH_2C\underline{H}_3$).

Example 3

Diethyl 4-t-Butylbenzylmalonate (1d)

74% yield, colorless oil; $^1$H NMR ($CDCl_3$) δ 7.29 (d, 2H), 7.13 (d, 2H), 4.16 (q, 4H, 2×$CO_2CH_2$), 3.63 (t, 1H, CH), 3.18 (d, 2H, CH$_2$Ar), 1.30 (s, 9H, C(CH$_3$)$_3$), 1.20 (t, 6H, 2×CO$_2$CH$_2$CH$_3$).

General Procedure for the Synthesis of 2a–d

A cooled solution of lithium aluminum hydride (3.64 g, 96 nmnol) in diethyl ether (80 mL) at 0° C. was treated dropwise with a solution of 1 (24 mmol) in diethyl ether (20 mL). After stirring for 3 h at room temperature, the reaction mixture was cooled over an ice-bath and treated by successively by the dropwise addition of 3.5 mL of H$_2$O, 7 ml of 15% NaOH solution, and 10.5 mL of H$_2$O. The mixture was filtered by washing with EtOAc and the filtrate was concentrated in vacuo. The residue was purified by flash column chromatography over silica gel with EtOAc/hexane (3:1) as eluant to give 2.

Example 4

2-Benzyl-1,3-propanediol (2a)

98% yield, white solid, mp=67° C.; $^1$H NMR (CDCl$_3$) δ 7.15–7.30 (m, 5H, phenyl), 3.74 (dd, 2H, CH$_2$OH), 3.62 (dd, 2H, CH$_2$OH), 2.9–3.0 (bs, 2H, OH), 2.58 (d, 2H, CH$_2$Ph), 2.03 (m, 1H, CH).

Example 5

2-(3,4-Dimethylbenzyl)-1,3-propandiol (2b)

92% yield, colorless oil; $^1$H NMR (CDCl$_3$) δ 6.88–7.06 (m, 3H, phenyl), 3.6–3.8 (m, 4H, 2×CH$_2$OH), 2.5–2.7 (bs, 2H, OH), 2.60 (d, 1H, CH$_2$Ph), 2.52 (d, 1H, CH$_{2Ph}$), 2.2–2.28 (m, 6H, 2×CH$_3$), 2.02 (m, 1H, CH).

Example 6

2-(4-Chlorobenzyl)-1,3-propandiol (2c)

75% yield, white solid, mp=64° C.; $^1$H NMR (CDCl$_3$) δ 7.24 (d, 2H), 7.10 (d, 2H), 3.75 (dd, 2H, CH$_2$OH), 3.61 (dd, 2H, CH$_2$OH), 2.85 (bs, 2H, OH), 2.58 (d, 2H, CH$_2$Ph), 1.97 (m, 1H, CH).

Example 7

2-(4-t-Butylbenzyl)-1,3-propandiol (2d)

80% yield, white solid, mp=67° C.; $^1$H NMR (CDCl$_3$) δ 7.31 (d, 2H), 7.11 (d, 2H), 3.81 (dd, 2H, CH$_2$OH), 3.68 (dd, 2H, CH$_2$OH), 2.58 (d, 2H, CH$_2$Ph), 2.23 (bs, 2H, OH), 2.05 (m, 1H, CH), 1.30 (s, 9H, C(CH$_3$)$_3$).

General Procedure for the Synthesis of 3a–d

A mixture of 2 (20 mmol), trimethylorthoacetate (3.6 g, 30 mmol) and a catalytic amount of p-toluenesulfonic acid in CH$_2$Cl$_2$ (40 mL) was stirred for 2 h at room temperature, and then treated with H$_2$O (0.54 g, 30 mmol). After stirring overnight at room temperature, the reaction mixture was concentrated in vacuo. The residue was purified by flash column chromatography over silica gel with EtOAc/hexane (1:2) as eluant to give 3.

Example 8

2-Benzyl-3-hydroxypropyl acetate (3a).

97% yield, colorless oil; $^1$H NMR (CDCl$_3$) δ 7.1–7.25 (m, 5H, phenyl), 4.06 (ddd of AB, 2H, CH$_2$OAc), 3.48 (m, 2H, CH$_2$OH), 2.58 (ddd of AB, 2H, CH$_2$Ph), 2.10 (m, 1H, CH), 2.01 (s, 3H, COCH$_3$).

Example 9

(R)-2-Benzyl-1,3-propanediol ((R)-3a)

This compound was obtained from 2a by a published literature procedure (Tetrahedron Letters 30, 6189–6192 (1989)).

Example 10

2-(3,4-Dimethylbenzyl)-3-hydroxypropyl Acetate (3b)

90% yield, colorless oil; $^1$H NMR (CDCl$_3$) δ 6.88–7.06 (m, 5H, phenyl), 4.13 (m, 2H, CH$_2$OAc), 3.54 (m, 2H, CH$_2$OH), 2.62 (m, 2H, CH$_2$Ph), 2.2–2.3 (m, 6H, 2×CH$_3$), 2.10 (m, 1H, CH), 2.07 (s, 3H, COCH$_3$).

Example 11

2-(4-Chlorobenzyl)-3-hydroxypropyl Acetate (3c)

86% yield, colorless oil; $^1$H NMR (CDCl$_3$) δ 7.25 (d, 2H), 7.12 (d, 2H), 4.12 (ddd of AB, 2H, CH$_2$OAc), 3.53 (ddd of AB, 2H, CH$_2$OH), 2.63 (ddd of AB, 2H, CH$_2$Ph), 2.10 (m, 1H, CH), 2.06 (s, 3H, COCH$_3$).

Example 12

2-(4-t-Butylbenzyl)-3-hydroxypropyl Acetate (3d)

84% yield, colorless oil; $^1$H NMR (CDCl$_3$) δ 7.30 (d, 2H), 7.11 (d, 2H), 4.13 (ddd of AB, 2H, CH$_2$OAc), 3.56 (ddd of AB, 2H, CH$_2$OH), 2.62 (ddd of AB, 2H, CH$_2$Ph), 2.28 (s, 1H, OH), 2.10 (m, 1H, CH), 2.01 (s, 3H, COCH$_3$), 1.30 (s, 9H, C(CH$_3$)$_3$).

General Procedure for the Synthesis of 4a–d

A cooled solution of 3 (12 mmol) and triethylamine (3.64 g, 36 mmol) in CH$_2$Cl$_2$ (20 mL) at 0° C. was treated dropwise with methanesulfonylchloride (2.06 g, 18 mmol). After stirring for 6 h at room temperature, the mixture was diluted with CH$_2$Cl$_2$. The organic layer was washed with 1 N HCl, H$_2$O and brine, dried over MgSO$_4$, and concentrated in vacuo. The residue was purified by flash column chromatography on silica gel with EtOAc/hexane (1:3) as eluant to give the corresponding mesylate as an oil. The mesylate was dissovled in DMF (10 mL) and treated with sodium azide (2.2 g, 34 mmol). After 8 h of stirring at 80° C., the reaction mixture was diluted with H$_2$O and extracted with EtOAc several times. The combined organic layer was washed with H$_2$O, dried over MgSO$_4$ and concentrated in vacuo. The residue was purified by flash column chromatography on silica gel with EtOAc/hexane (1:15) as eluant to give 4.

Example 13

3-Azido-2-benzylpropyl Acetate (4a)

92% yield, colorless oil; $^1$H NMR (CDCl$_3$) δ 7.15–7.35 (m, 5H, phenyl), 4.05 (ddd of AB, 2H, CH$_2$OAc), 3.34 (m, 2H, CH$_2$N$_3$), 2.68 (d, 2H, CH$_2$Ph), 2.22 (m, 1H, CH), 2.08 (s, 3H, COCH$_3$).

Example 14

3-Azido-2-(3,4-dimethylbenzyl)propyl Acetate (4b)

85% yield, colorless oil; $^1$H NMR (CDCl$_3$) δ 6.87–7.07 (m, 3H), 4.04 (m, 2H, CH$_2$OAc), 3.33 (m, 2H, CH$_2$N$_3$), 2.69

(d, 1H, CH$_2$Ph), 2.60 (d, 1H, CH$_2$Ph), 2.1–2.3 (m, 7H, 2×CH$_3$ and CH), 2.07 (s, 3H, COCH$_3$).

Example 15

3-Azido-2-(4-chlorobenzyl)propyl Acetate (4c)

88% yield, colorless oil; $^1$H NMR (CDCl$_3$) δ 7.26 (d, 2H), 7.12 (d, 2H), 4.03 (ddd of AB, 2H, CH$_2$OAc), 3.34 (m, 2H, CH$_2$N$_3$), 2.65 (d, 2H, CH$_2$Ph), 2.17 (m, 1H, CH), 2.07 (s, 3H, COCH$_3$).

Example 16

3-Azido-2-(4-t-butylbenzyl)propyl Acetate (4d)

92% yield, colorless oil; $^1$H NMR (CDCl$_3$) δ 7.32 (d, 2H), 7.08 (d, 2H), 4.05 (ddd of AB, 2H, CH$_2$OAc), 3.35 (ddd of AB, 2H, CH$_2$N$_3$), 2.64 (d, 2H, CH$_2$Ph), 2.20 (m, 1H, CH), 2.07 (s, 3H, COCH$_3$), 1.30 (s, 9H, C(CH$_3$)$_3$).

General Procedure for the Synthesis of 5a–d

A solution of 4 (8 mmol) and a catalytic amount of K$_2$CO$_3$ in MeOH (10 mL) was treated with a couple of drops of H$_2$O. After stirring for 2 h at room temperature, the reaction mixture was quenched with several drops of acetic acid and concentrated in vacuo. The residue was purified by flash column chromatography on silica gel with EtOAc/hexane (1:3) as eluant to give 5.

Example 17

3-Azido-2-benzyl-1-propanol (5a)

98% yield, colorless oil; $^1$H NMR (CDCl$_3$) δ 7.15–7.35 (m, 5H, phenyl), 3.65 (m, 2H, CH$_2$OH), 3.40 (ddd of AB, 2H, CH$_2$N$_3$), 2.67 (ddd of AB, 2H, CH$_2$Ph), 2.04 (m, 1H, CH).

Example 18

3-Azido-2-(3,4-dimethylbenzyl)-1-propanol (5b)

92% yield, colorless oil; $^1$H NMR (CDCl$_3$) δ 6.88–7.08 (m, 5H, phenyl), 3.65 (m, 2H, CH$_2$OH), 3.42 (m, 2H, CH$_2$N$_3$), 2.68 (dd, 1H, CH$_2$Ph), 2.60 (dd, 1H, CH$_2$Ph), 2.2–2.3 (m, 6H, 2×CH$_3$), 2.03 (m, 1H, CH).

Example 19

3-Azido-2-(4-chlorobenzyl)-1-propanol (5c)

88% yield, colorless oil; $^1$H NMR (CDCl$_3$) δ 7.25 (d, 2H), 7.10 (d, 2H), 3.58 (m, 2H, CH$_2$OH), 3.36 (m, 2H, CH$_2$N$_3$), 2.63 (dd, 2H, CH$_2$Ph), 2.1 (bs, 1H, OH), 1.98 (m, 1H, CH).

Example 20

3-Azido-2-(4-t-butylbenzyl)-1-propanol (5d)

98% yield, colorless oil; $^1$H NMR (CDCl$_3$) δ 7.32 (d, 2H), 7.10 (d, 2H), 3.63 (ddd of AB, 2H, CH$_2$OH), 3.39 (ddd of AB, 2H, CH$_2$N$_3$), 2.62 (m, 2H, CH$_2$Ph), 2.02 (m, 1H, CH), 1.78 (bs, 1H, OH), 1.30 (s, 9H, C(CH$_3$)$_3$).

General Procedure for the Synthesis of 6a–d

A cooled solution of 5 (1 mmol), triethylarnine (4 mmol) and a catalytic amount of 4-dimethylaminopyridine in CH$_2$Cl$_2$ (5 mL) at 0° C. was treated with the corresponding acyl chloride (2 mmol). After 2–12 h of stirring at room temperature, the mixture was diluted with CH$_2$Cl$_2$. The organic layer was washed with 1 N HCl, H$_2$O and brine, dried over MgSO$_4$, and concentrated in vacuo. The residue was purified by flash column chromatography over silica gel with EtOAc/hexane (1:10–20) as eluant to give 6.

Example 21

3-Azido-2-benzylpropyl Pivalate (6a-I)

92% yield, colorless oil; $^1$H NMR (CDCl$_3$) δ 7.15–7.35 (m, 5H, phenyl), 4.04 (ddd of AB, 2H, CH$_2$OCO), 3.34 (ddd of AB, 2H, CH$_2$N$_3$), 2.68 (d, 2H, CH$_2$Ph), 2.21 (m, 1H, CH), 1.23 (s, 9H, C(CH3)$_3$).

Example 22

3-Azido-2-benzylpropyl 2-Methylpropanoate (6a-II)

93% yield, colorless oil; $^1$H NMR (CDCl$_3$) δ 7.15–7.35 (m, 5H, phenyl), 4.05 (ddd of AB, 2H, CH$_2$OCO), 3.34 (m, 2H, CH$_2$N$_3$), 2.68 (d, 2H, CH$_2$Ph), 2.58 (m, 1H, CHMe$_2$), 2.21 (m, 1H, CH), 1.18 (dd, 6H, 2×CH$_3$).

Example 23

3-Azido-2-benzylpropyl Hexanoate (6a-III)

90% yield, colorless oil; $^1$H NMR (CDCl$_3$) δ 7.14–7.35 (m, 5H, phenyl), 4.05 (ddd of AB, 2H, CH$_2$OCO), 3.34 (m, 2H, CH$_2$N$_3$), 2.68 (d, 2H, CH$_2$Ph), 2.32 (t, 2H, OOCCH$_2$), 2.20 (m, 1H, CH), 1.64 (m, 2H), 1.2–1.4 (m, 4H), 0.88 (distorted t, 3H).

Example 24

3-Azido-2-benzylpropyl Stearate (6a-IV)

78% yield, colorless oil; $^1$H NMR (CDCl$_3$) δ 7.14–7.35 (m, 5H, phenyl), 4.05 (ddd of AB, 2H, CH$_2$OCO), 3.33 (m, 2H, CH$_2$N$_3$), 2.68 (d, 2H, CH$_2$Ph), 2.32 (t, 2H, OOCCH$_2$), 2.20 (m, 1H, CH), 1.2–1.7 (m, 30 H), 0.88 (distorted t, 3H).

Example 25

3-Azido-2-benzylpropyl Benzoate (6a-V)

90% yield, colorless oil; $^1$H NMR (CDCl$_3$) δ 8.04 (m, 2H), 7.15–7.60 (m, 8H), 4.35 (dd, 1H, J=5.1 and 11.2 Hz, BzOCH$_2$), 4.26 (dd, 1H, BzOCH$_2$), 3.43 (ddd of AB, 2H, J=5.61, 5.85 and 12.42 Hz, CH$_2$N$_3$), 2.78 (m, 2H, CH$_2$Ph), 2.35 (mn, 1H, CH).

Example 26

3-Azido-2-(3,4-dimethylbenzyl)propyl Pivalate (6b-I)

94% yield, colorless oil; $^1$H NMR (CDCl$_3$) δ 6.86–7.07 (m, 3H), 4.04 (m, 2H, CH$_2$OCO), 3.36 (m, 2H, CH$_2$N$_3$), 2.70 (d, 1H, CH$_2$Ph), 2.61 (d, 1H, CH$_2$Ph), 2.1–2.3 (m, 7H, 2×CH$_3$ and CH), 1.23 (s, 9H, C(CH$_3$)$_3$).

Example 27

3-Azido-2-(3,4-dimethylbenzyl)propyl Benzoate (6b-V)

95% yield, colorless oil; $^1$H NMR (CDCl$_3$) δ 8.02 (m, 2H), 7.57 (m, 1H), 7.46 (m, 2H), 6.8–7.07 (m, 3H), 4.32 (m, 2H, CH$_2$OCO), 3.45 (m, 2H, CH$_2$N$_3$), 2.80 (d, 1H, CH$_2$Ph), 2.71 (d, 1H, CH$_2$Ph), 2.2–2.4 (m, 7H, 2×CH$_3$ and CH).

Example 28

3-Azido-2-(3,4-dimethylbenzyl)propyl 3,4-Dimethylbenzoate (6b-VI)

84% yield, colorless oil; $^1$H NMR (CDCl$_3$) δ 7.77 (m, 2H), 7.21 (m, 1H), 6.9–7.07 (m, 3H), 4.30 (m, 2H, CH$_2$OCO), 3.44 (m, 2H, CH$_2$N$_3$), 2.79 (d, 1H, CH$_2$Ph), 2.70 d, 1H, CH$_2$Ph), 2.2–2.4 (m, 13 H, 4×CH$_3$ and CH).

Example 29

3-Azido-2-(4-chlorobenzyl)propyl Pivalate (6c-I)

86% yield, colorless oil; $^1$H NMR (CDCl$_3$) δ 7.27 (d, 2H), 7.09 (d, 2H), 4.02 (ddd of AB, 2H, CH$_2$OCO), 3.33 (m, 2H, CH$_2$N$_3$), 2.66 (d, 2H, CH$_2$Ph), 2.18 (m, 1H, CH), 1.23 (s, 9H, C(CH$_3$)$_3$).

Example 30

3-Azido-2-(4-chlorobenzyl)propyl Benzoate (6c-V)

92% yield, colorless oil; $^1$H NMR (CDCl$_3$) δ 8.01 (m, 2H), 7.58 (m, 1H), 7.46 (m, 2H), 7.28 (d, 2H), 7.13 (d, 2H), 4.29 (ddd of AB, 2H, CH$_2$OCO), 3.43 (m, 2H, CH$_2$N$_3$), 2.75 (d, 2H, CH$_2$Ph), 2.33 (m, 1H, CH).

Example 31

3-Azido-2-(4-t-butylbenzyl)propyl Pivalate (6d-I)

99% yield, colorless oil; $^1$H NMR (CDCl$_3$) δ 7.31 (d, 2H), 7.08 (d, 2H), 4.04 (ddd of AB, 2H, CH$_2$OCO), 3.35 (m, 2H, CH$_2$N$_3$), 2.65 (d, 2H, CH$_2$Ph), 2.20 (m, 1H, CH), 1.30 (s, 9H, C(CH$_3$)$_3$), 1.23 (s, 9H, C(CH$_3$)$_3$).

Example 32

3-Azido-2-(4-t-butylbenzyl)propyl Benzoate (6d-V)

88% yield, colorless oil; $^1$H NMR (CDCl$_3$) δ 8.04 (m, 2H), 7.57 (m, 1H), 7.45 (m, 2H), 7.32 (d, 2H), 7.12 (d, 2H), 4.31 (ddd of AB, 2H, CH$_2$OCO), 3.44 (m, 2H, CH$_2$H$_3$), 2.75 (d, 2H, CH$_2$Ph), 2.35 (m, 1H, CH), 1.30 (s, 9H, C(CH$_3$)$_3$).

General Procedure for the Synthesis of 7a–d

A solution of 6 (0.5 mmol) and Lindler's catalyst (50 mg) in EtOH (5 mL) was hydrogenated under a hydrogen balloon for 2 h. The reaction mixture was filtered and the filtrate was concentrated in vacuo. The residue was dissolved in CH$_2$Cl$_2$ (5 mL) and treated with 4-[(methoxyhnethyl)oxy)]-3-methoxybenzyl isothiocyanate (0.5 mmol). After stirring overnight at room temperature, the reaction mixture was concentrated and the residue was purified by flash column chromatography on silica gel with EtOAc/hexane (1:1) as eluant to give the corresponding thiourea. The thiourea was dissolved in CH$_2$Cl$_2$ (2 mL) and treated with trifluoroacetic acid (1 mL). After 1 hr of stirring at room temperature, the mixture was quenched with solid NaHCO$_3$, filtered, and the filtrate was concentrated. The residue was diluted with EtOAc, washed with NaHCO$_3$, H$_2$O and brine, and concentrated in vacuo. The residue was purified by flash column chromatography on silica gel with EtOAc/hexane (1:1) as eluant to give 7.

Example 33

2-Benzyl-3-{[(4-hydroxy-3-methoxybenzyl)amino]carbothioyl}propyl Pivalate (7a-I)

40% yield, colorless oil; $^1$H NMR (CDCl$_3$) δ 7.1–7.32 (m, 5H, phenyl), 6.75–6.9 (m, 3H, Ar), 6.27 (bt, 1H, NH), 6.05 (bs, 1H, NH), 5.63 (s, 1H, OH), 4.40 (bd, 2H, J=4.38 Hz, NHCH$_2$Ar), 4.17 (dd, 1H, J=3.9 and 11.46 Hz, CH$_2$OCO), 3.87 (s, 3H, OCH$_3$), 3.7–3.85 (m, 2H, 1H of CH$_2$OCO and CHCH$_2$NHC=S), 3.24 (ddd, 1H, J=5.37, 8.07 and 13.89 Hz, CHCH$_2$NHC=S), 2.61 (ddd of AB, 2H, CH$_2$Ph), 2.33 (m, 1H, CH), 1.23 (s, 9H, C(CH$_3$)$_3$); IR (neat): 3362, 1715, 1278, 1157; MS m/e 445 (M$^+$+1). Anal. (C$_{24}$H$_{32}$N$_2$O$_4$S) C, H, N, S.

Example 34

(R)-2-Benzyl-3-{[(4-hydroxy-3-methoxybeiazyl)amino]carbothioyl}propyl Pivalate ((R)-7a-I)

(R)-enantiomer of 7a-I; This compound was obtained from (R)-3a following the same general procedure for 7a-I; [α]$_D$=−714 (c, 0.22, CHCl$_3$).

Example 35

(S)-2-Benzyl-3-{[(4-hydroxy-3-methoxybenzyl)amino]carbothioyl}propyl Pivalate ((S)-7a-I)

(S)-enantiomer of 7a-I; This compound was obtained from (R)-3a following the same general procedure for 7a-I; [α]$_D$=+695 (c, 0.08, CHCl$_3$).

Example 36

2-Benzyl-3-{[(4-hydroxy-3-methoxybenzyl)amino]carbothioyl}propyl 2-Methyl Propanoate (7a-II)

35% yield, colorless oil; $^1$H NMR (CDCl$_3$) δ 7.13–7.30 (m, 5H, phenyl), 6.75–6.87 (m, 3H, Ar), 6.34 (bt, 1H, NH), 6.30 (bs, 1H, NH), 5.75 (s, 1H, OH), 4.40 (bs, 2H, NHCH$_2$Ar), 4.17 (dd, 1H, J=3.9 and 10.95 Hz, CH$_2$OCO), 3.84 (s, 3H, OCH$_3$), 3.65–3.85 (m, 2H, CH$_2$OCO and CHCH$_2$NHC=S), 3.28 (m, 1H, CHCH$_2$NHC=S), 2.60 (m, 3H, CH$_2$Ph and CHMe$_2$), 2.30 (m, 1H, CHCH$_2$Ph), 1.18 (dd, 6H, 2×CH$_3$); IR (neat): 3361, 1715, 1273, 1157; MS m/e 430 (M$^+$). Anal. (C$_{23}$H$_{30}$N$_2$O$_4$S) C, H, N, S.

Example 37

2-Benzyl-3-{[(4-hydroxy-3-methoxybenzyl)amino]carbothioyl}propyl Hexanoate (7a-III)

34% yield, colorless oil; $^1$H NMR (CDCl$_3$) δ 7.1–7.3 (m, 5H, phenyl), 6.75–6.9 (m, 3H, Ar), 6.23 (bt, 1H, NH), 6.11 (bs, 1H, NH), 5.66 (s, 1H, OH), 4.40 (bs, 2H, NHCH$_2$Ar), 4.15 (dd, 1H, J=3.9 and 11.43 Hz, CH$_2$OCO), 3.86 (s, 3H, OCH$_3$), 3.65–3.85 (m, 2H, CH$_2$OCO and CHCH$_2$NHC=S), 3.29 (m, 1H, CHCH$_2$NHC=S), 2.61 (m, 2H, CH$_2$Ph), 2.30 (m, 3H, CH$_2$COO and CH), 1.65 (m, 2H), 1.2–1.4 (m, 4H), 0.88 (distorted t, 3H); IR (neat): 3360, 1715, 1274, 1122; MS m/e 458 (M$^+$). Anal. (C$_{25}$H$_{34}$N$_2$O$_4$S) C, H, N, S.

Example 38

2-Benzyl-3-{[(4-hydroxy-3-methoxybenzyl)amino]carbothioyl}propyl Stearate (7a-IV)

30% yield, colorless oil; $^1$H NMR (CDCl$_3$) δ 7.1–7.3 (m, 5H, phenyl), 6.75–6.9 (m, 3H, Ar), 6.28 (bt, 1H, NH), 6.17 (bs, 1H, NH), 5.69 (s, 1H, OH), 4.39 (bs, 2H, NHCH$_2$Ar), 4.14 (dd, 1H, J=3.9 and 11.67 Hz, CH$_2$OCO), 3.87 (s, 3H, OCH$_3$), 3.65–3.85 (m, 2H, CH$_2$OCO and CHCH$_2$NHC=S), 3.30 (m, 1H, CHCH$_2$NHC=S), 2.60 (m, 2H, CH$_2$Ph), 2.30 (m, 3H, CH$_2$COO and CH), 1.2–1.7 (m, 30H), 0.88 (distorted t, 3H); IR (neat): 3363, 1731, 1274, 1031; MS m/e 626 (M$^+$). Anal. (C$_{37}$H$_{58}$N$_2$O$_4$S)

Example 39

2-Benzyl-3-{[(4-hydroxy-3-methoxybenzyl)amino]carbothioyl}propyl Benzoate (7a-V)

50% yield, white solid, mp=90° C.; $^1$H NMR (CDCl$_3$) δ 7.98–8.02 (m, 2H), 7.58 (mn, 1H), 7.4–7.5 (m, 2H), 7.1–7.32 (m, 5H, phenyl), 6.72–6.85 (m, 3H, Ar), 6.42 (bt, 1H, NH), 6.31 (bs, 1H, NH), 5.73 (s, 1H, OH), 4.34–4.42 (m, 3H, NHCH$_2$Ar and CH$_2$OCO), 4.05 (dd, 1H, CH$_2$OCO), 3.7–3.85 (m, 4H, OCH$_3$ and CHCH$_2$NHC=S), 3.38 (m, 1H, CHCH$_2$NHC=S), 2.6–2.78 (m, 2H, CH$_2$Ph), 2.46 (m, 1H, CH); IR (neat): 3360, 1714, 1274, 1121; MS m/e 464 (M$^+$). Anal. (C$_{26}$H$_{28}$N$_2$O$_4$S) C, H, N, S.

Example 40

2-(3,4-Dimethylbenzyl)-3-{[(4-hydroxy-3-methoxybenzyl)amino]carbothioyl}propyl Pivalate (7b-I)

40% yield, white solid, mp=47° C.; $^1$H NMR (CDCl$_3$) δ 6.93–7.05 (m, 3H), 6.77–6.9 (m, 3H, Ar), 6.22 (m, 1H, NH), 5.98 (bs, 1H, NH), 5.61 (s, 1H, OH), 4.37 (bs, 2H, NHCH$_2$Ar), 4.17 (ddd of AB, 1H, CH$_2$OCO), 3.87 (s, 3H, OCH$_3$), 3.7–3.85 (m, 2H, CH$_2$OCO and CHCH$_2$NHC=S), 3.27 (m, 1H, CHCH$_2$NHC=S), 2.60 (m, 2H, CH$_2$Ph), 2.2–2.32 (m, 7H, 2×CH$_3$ and CH), 1.22 (s, 9H, C(CH$_3$)$_3$); IR (neat): 3360, 1714, 1279, 1159; MS m/e 474 (M$^+$+2). Anal. (C$_{26}$H$_{36}$N$_2$O$_4$S) C, H, N, S.

Example 41

2-(3,4-Dimethylbenzyl)-3-{[(4-hydroxy-3-methoxybenzyl)amino]carbothioyl}propyl benzoate (7b-V)

45% yield, white solid, mp=44° C.; $^1$H NMR (CDCl$_3$) δ 8.02 (m, 2H), 7.59 (m, 1H), 7.46 (m, 2H), 6.9–7.06 (m, 3H), 6.72–6.85 (m, 3H, Ar), 6.33 (m, 1H, NH), 6.13 (bs, 1H, NH), 5.65 (s, 1H, OH), 4.35–4.44 (m, 3H, NHCH$_2$Ar and CH$_2$OCO), 4.05 (m, 1H, CH$_2$OCO), 3.7–3.85 (m, 4H, OCH$_3$ and CHCH$_2$NHC=S), 3.40 (m, 1H, CHCH$_2$NHC=S), 2.6–2.78 (m, 2H, CH$_2$Ph), 2.44 (m, 1H, CH), 2.2–2.3 (m, 6H, 2×CH$_3$); IR (neat): 3360, 1713, 1274, 1121; MS m/e 492 (M$^+$). Anal. (C$_{28}$H$_{32}$N$_2$O$_4$S) C, H, N, S.

Example 42

2-(3,4-Dimethylbenzyl)-3-{[(4-hydroxy-3-methoxybenzyl)amino]carbothioyl}propyl 3,4-Dimethylbenzoate (7b-VI)

55% yield, white solid, mp=58° C.; $^1$H NMR (CDCl$_3$) δ 7.75 (m, 2H), 7.20 (m, 1H), 6.9–7.06 (m, 3H), 6.74–6.85 (m, 3H, Ar), 6.39 (m, 1H, NH), 6.07 (bs, 1H, NH), 5.63 (s, 1H, OH), 4.35–4.43 (m, 3H, NHCH$_2$Ar and CH$_2$OCO), 4.05 (m, 1H, CH$_2$OCO), 3.7–3.85 (m, 4H, OCH$_3$ and CHCH$_2$NHC=S), 3.37 (m, 1H, CHCH$_2$NHC=S), 2.6–2.74 (m, 2H, CH$_2$Ph), 2.41 (m, 1H, CH), 2.2–2.35 (m, 12H, 4×CH$_3$); IR (neat): 3373, 1711, 1266, 1124; MS m/e 520 (M$^+$). Anal. (C$_{30}$H$_{36}$N$_2$O$_4$S) C, H, N, S.

Example 43

2-(4-Chlorobenzyl)-3-{[(4-hydroxy-3-methoxybenzyl)amino]carbothioyl}propyl Pivalate (7c-I)

40% yield, white solid, mp=62° C.; $^1$H NMR (CDCl$_3$) δ 7.25 (d, 2H), 7.10 (d, 2H), 6.77–6.90 (m, 3H, Ar), 6.38 (t, 1H, NH), 6.25 (bs, 1H, NH), 5.72 (s, 1H, OH), 4.42 (bs, 2H, NHCH$_2$Ar), 4.16 (dd of AB, 1H, CH$_2$OCO), 3.86 (s, 3H, OCH$_3$), 3.7–3.85 (m, 2H, CH$_2$OCO and CHCH$_2$NHC=S), 3.19 (m, 1H, CHCH$_2$NHC=S), 2.59 (ddd of AB, 2H, CH$_2$Ph), 2.32 (m, 1H, CH), 1.22 (s, 9H, C(CH$_3$)$_3$); IR (neat): 3360, 1714, 1279, 1159; MS m/e 479 (M$^+$). Anal. (C$_{24}$H$_{31}$ClN$_2$O$_4$S) C, H, N, S.

Example 44

2-(4-Chlorobenzyl)-3-{[(4-hydroxy-3-methoxybenzyl)amino]carbothioyl}propyl Benzoate (7c-V)

55% yield, white solid, mp=57° C.; $^1$H NMR (CDCl$_3$) δ 8.00 (m, 2H), 7.60 (m, 1H), 7.47 (m, 2H), 7.27 (d, 2H), 7.15 (d, 2H), 6.76–6.90 (m, 3H, Ar), 6.36 (t, 1H, NH), 6.15 (bs, 1H, NH), 5.61 (s, 1H, OH), 4.40 (m, 3H, NHCH$_2$Ar and CH$_2$OCO), 4.00 (dd of AB, 1H, CH$_2$OCO), 3.86 (s, 3H, OCH$_3$), 3.85 (m, 1H, CHCH$_2$NHC=S), 3.31 (m, 1H, CHCH$_2$NHC=S), 2.67 (ddd of AB, 2H, CH$_2$Ph), 2.46 (m, 1H, CH); IR (neat): 3373, 1711, 1266, 1124; MS m/e 499 (M$^+$). Anal. (C$_{26}$H$_{27}$ClN$_2$O$_4$S) C, H, N, S.

Example 45

2-(4-t-Butylbenzyl)-3-{[(4-hydroxy-3-methoxybenzyl)amino]carbothioyl}propyl Pivalate (7d-I)

40% yield, yellow solid, mp=52° C.; $^1$H NMR (CDCl$_3$) δ 7.30 (d, 2H), 7.09 (d, 2H), is 6.75–6.90 (m, 3H, Ar), 6.27 (t, 1H, NH), 6.10 (bs, 1H, NH), 5.66 (s, 1H, OH), 4.40 (bs, 2H, NHCH$_2$Ar), 4.15 (dd of AB, 1H, CH$_2$OCO), 3.86 (s, 3H, OCH$_3$), 3.7–3.85 (m, 2H, CH$_2$OCO and CHCH$_2$NHC=S), 3.27 (m, 1H, CHCH$_2$NHC=S), 2.58 (ddd of AB, 2H, CH$_2$Ph), 2.30 (m, 1H, CH), 1.29 (s, 9H, C(CH$_3$)$_3$), 1.22 (s, 9H, C(CH$_3$)$_3$); IR (neat): 3360, 1714, 1277, 1158; MS m/e 500 (M$^+$). Anal. (C$_{28}$H$_{40}$N$_2$O$_4$S), C, H, N, S.

Example 46

2-(4-t-Butylbenzyl)-3-{[(4-hydroxy-3-methoxybenzyl)amino]carbothioyl}propyl Benzoate (7d-V)

50% yield, white solid, mp=54° C.; $^1$H NMR (CDCl$_3$) δ 8.02 (m, 2H), 7.60 (m, 1H), 7.46 (m, 2H), 7.32 (d, 2H), 7.14 (d, 2H), 6.75–6.90 (m, 3H, Ar), 6.28 (t, 1H, NH), 6.06 (bs, 1H, NH), 5.61 (s, 1H, OH), 4.40 (m, 3H, NHCH$_2$Ar and CH$_2$OCO), 4.08 (dd of AB, 1H, CH$_2$OCO), 3.86 (s, 3H, OCH$_3$), 3.80 (m, 1H, CHCH$_2$NHC=S), 3.40 (m, 1H, CHCH$_2$NHC=S), 2.68 (m, 2H, CH$_2$Ph), 2.46 (m, 1H, CH), 1.29 (s, 9H, C(CH$_3$)$_3$); IR (neat): 3360, 1714, 1272, 1124; MS m/e 520 (M$^+$). Anal. (C$_{30}$H$_{36}$N$_2$O$_4$S) C, H, N, S.

Example 47

N-[2-Benzyl-3-(benzyloxy)propyl]-N'-(4-hydroxy-3-methoxybenzyl)thiourea (9a)

60% yield, colorless oil; $^1$H NMR (CDCl$_3$) δ 7.10–7.30 (m, 10 H, 2×Ph), 6.81 (d, 1H, Ar), 6.60 (bs, 1H, Ar), 6.56 (d, 1H, Ar), 6.54 (bs, 1H, NH), 5.64 (s, 1H, OH), 4.35 (m, 4H, NHCH$_2$Ar and PhCH$_2$O), 3.82 (s, 3H, OCH$_3$), 3.50 (m, 2H, BnOCH$_2$), 3.37 (bt, 2H, CHCH$_2$NHC=S), 2.64 (m, 2H, CH$_2$Ph), 2.20 (m, 1H, CH); IR (neat): 3288, 1274, 1123; MS m/e 450 (M$^+$). Anal. (C$_{26}$H$_{30}$N$_2$O$_3$S) C, H, N, S.

Example 48

N-[3-Benzyloxy-2-(4-chlorobenzyl)propyl]-N'-(4-hydroxy-3-methoxybenzyl)thiourea (9c)

White solid, mp=37.5° C.; $^1$H NMR (CDCl$_3$) δ 7.0–7.3 (m, 9H), 6.5–6.84 (m, 3H, Ar), 6.54 (bs, 1H, NH), 6.30 (bs, 1H, NH), 5.68 (s, 1H, OH), 4.32 (m, 4H, NHCH$_2$Ar and PhCH$_2$O), 3.82 (s, 3H, OCH$_3$), 3.48 (m, 2H, BnOCH$_2$), 3.34 (m, 2H, CHCH$_2$NHC=S), 2.58 (m, 2H, CH$_2$Ph), 2.16 (m, 1H, CH); IR (neat): 3340, 1273, 1153; MS m/e 484 (M$^+$). Anal. (C$_{26}$H$_{29}$ClN$_2$O$_3$S) C, H, N, S.

Example 49

3-Methoxy-4-methoxymethoxy-benzonitrile (12)

A solution of 4-hydroxy-3-methoxy-benzonitrile (11, 1.5 g, 10 mmol) and diisopropylethylamine (2.7 mL, 15 mmol) in CH$_2$Cl$_2$ (50 mL) was treated with chloromethylmethyl-ether (0.92 mL, 12 mmol) and stirred for 3 h. After diluted with CH$_2$Cl$_2$, the mixture was washed with H$_2$O, dried over MgSO$_4$ and concentrated in vacuo. The residue was purified by flash column chromatography over silica gel using EtOAc:Hex (1:2) as eluant to give 12 as white solid (1.54 g, 80%).

$^1$H NMR (CDCl$_3$) δ 7.27 (s, 1H, Ar), 7.24 (s, 1H, Ar), 7.11(s, 1H, Ar), 5.29 (s, 2H, ArOCH$_2$), 3.99 (s, 3H, ArOCH$_3$), 3.51 (s, 3H, CH$_2$OCH$_3$).

Example 50

(3-Methoxy-4-methoxymethoxy benzyl)carbamic Acid Benzyl Ester (13)

A solution of 12 (1.54 g, 8 mmol) in THF (20 mL) was added dropwise to a stirred suspension of lithiumaluminum hydride (1.2 g, 32 mmnol) in THF (30 mL). After refluxed for 4 h, the reaction mixture was cooled to 0° C. and quenched with 5 N NaOH to destroy excess LiAlH$_4$. Precipitated aluminum salts were removed by filtration and the THF was evaporated. The residue was partitioned with ether and H$_2$O. The ether layer was washed with brine, dried over K$_2$CO$_3$, filtered and concentrated in vacuo to give amine. The amine was dissolved in CH$_2$Cl$_2$ (15 mL) and the solution was treated with NEt$_3$ (1.16 mL, 8.3 mmol) and benzylchloro formate (1.18 mL, 8.3 mmol). After stirring for 2 h at room temperature, the reaction mixture was diluted with CH$_2$Cl$_2$. The organic layer was washed with H$_2$O and brine, dried over MgSO$_4$ and concentrated in vacuo. The residue was purified by flash column chromatography over silica gel using EtOAc:Hex (1:2) as eluant to give 13 as white solid (0.795 g, 30%).

$^1$H NMR (CDCl$_3$) δ 7.34 (m, 5H, phenyl), 7.08 (d, 1H, Ar), 6.81(m, 2H, Ar), 5.21 (s, 2H, ArOCH$_2$), 5.14 (s, 2H, OCH$_2$Ph), 4.32 (d, 2H, NH$_2$COO), 3.85 (s, 3H, ArOCH$_3$), 3.50 (s, 3H, ArOCH$_2$OCH$_3$).

Example 51

(4-Hydroxy-3-methoxybenzyl)carbamic Acid Benzyl Ester (14)

A solution of 13 (0.795 g, 2.4 mmol) in CH$_2$Cl$_2$ (5 mL) was treated with trifluoroacetic acid (2.5 mL) slowly and stirred for 5 min at room temperature. After cooling to 0° C., the reaction mixture was neutralized with saturated NaHCO$_3$ solution, diluted with H$_2$O and extracted with CH$_2$Cl$_2$ several times. The combined organic layer was washed with H$_2$O and brine, dried over MgSO$_4$ and concentrated in vacuo. The residue was purified by flash column chromatography over silica gel using EtOAc:Hex (2:1) as eluant to give 14 as white solid (680 mg, 99%).

$^1$H NMR (CDCl$_3$) δ 7.34 (m, 5H, phenyl), 6.83 (m, 3H, Ar), 5.14 (s, 2H, OCH$_2$Ph), 4.30 (d, 2H, NH$_2$COO), 3.86 (s, 3H, ArOCH$_3$).

Example 52

[4-(Benzyloxycarbonylamino-methyl)-2-methoxy-phenoxy]-acetic Acid Methyl Ester (15)

A solution of 14 (0.287 g, 1 mmol) in acetone (20 mL) was treated with K$_2$CO$_3$ (0.552 g, 4 mmol) and methyl bromoacetate (0.14 mL, 1.5 mmol) and refluxed for 3 h. After cooling, the reaction mixture was filtered and the filtrate was concentrated in vacuo. The residue was purified by flash column chromatography over silica gel using EtOAc:Hex (3:2) as eluant to give 15 as white solid (0.323 g, 90%).

$^1$H NMR (CDCl$_3$) δ 7.28–7.33 (m, 5H, phenyl), 6.78 (m, 3H, Ar), 5.11 (s, 2H, COCH$_2$Ph), 4.76 (s, 2H, CH$_2$Ph), 4.28 (d, 2H, CH$_2$NHCO), 3.81 (s, 3H, ArOCH$_3$), 3.76 (s, 3H, COOCH$_3$).

Example 53

[4-(Benzyloxycarbonylamino-methyl)-2-methoxy-phenoxyl-acetic Acid (16)

A solution of 5 (0.323 g, 0.9 mmol) in THF (1 mL) was treated with 15% NaOH solution (1 mL) and stirred for 30 min at room temperature. The reaction mixture was neutralized with acetic acid, diluted with H$_2$O and extracted with CH$_2$Cl$_2$ several times. The combined organic layer was washed with H$_2$O, dried over MgSO$_4$ and concentrated in vacuo to give 16 as white solid (0.276 g, 89%).

$^1$H NMR (DMSO) δ 7.72 (s, 1H, COOH), 7.17–7.33 (m, 5H, phenyl), 6.81(s, 1H, Ar), 6.67 (s, 2H, Ar), 5.02 (s, 2H, COCH$_2$Ph), 4.16 (s, 2H, CH$_2$Ph), 4.09 (d, 2H, CH$_2$NHCO), 3.70 (s, 3H, ArOCH$_3$).

Example 54

(4-Aminomethyl-2-methoxy-phenoxy)acetic Acid (17)

A solution of 16 (0.276 g, 0.8 mmol) in MeOH (5 mL) was treated with 10% palladium on carbon (30 mg) and hydrogenated under a balloon of hydrogen for 30 min. The reaction mixture was filtered and the filtrate was concentrated to give 17 as white solid (0.093 g, 55%) which was used to next step without further purification.

General Procedure for the Synthesis of 19

A solution of 17 (0.5 mmol) in DMF (1 mL) was treated with NEt$_3$ (1.0 mmol), stirred for 30 min and treated with a solution of isothiocyanate 18 (0.5 mmol) in DMF. After stirring for 24 h at room temperature, the reaction mixture was diluted with H$_2$O and extracted with EtOAc several times. The combined organic layer was washed H$_2$O and brine, dried over MgSO$_4$ and concentrated in vacuo. The residue was purified by flash column chromatography over silica gel using CH$_2$Cl$_2$:MeOH:AcOH (100:10:0.5) as eluant to give 19.

Example 55

2,2-Dimethyl-propionic Acid 2-[3-(4-Carboxymethoxy-3-methoxy-benzyl)-thioureidomethyl]-3-(3,4-dimethyl-phenyl)-propyl Ester (19a)

Yield 27%, white solid; $^1$H NMR (CDCl$_3$) δ 7.15–7.26 (m, 4H, Ar), 6.76 (m, 3H, Ar), 6.54 (m, 1H, NH), 4.53 (s, 2H, CH$_2$COOH), 4.45 (bs, 2H, NHCH$_2$Ar), 4.15 (ddd of AB, 1H, CH$_2$OC=O), 3.82 (s, 3H, OCH$_3$), 3.6–3.85 (m, 2H, CH$_2$OC=O and CHCH$_2$NHC=S), 3.26 (m, 1H, CHCH$_2$NHC=S), 2.60 (m, 2H, CH$_2$Ph), 2.20–2.28 (m, 7H, 2×CH$_3$ & CHCH$_2$Ph), 1.23 (s, 9H, CO(CH$_3$)$_3$).

Example 56

2,2-Dimethyl-propionic Acid 3-(4-t-Butyl-phenyl)-2-[3-(4-carboxymethoxy-3-methoxy-benzyl)-thioureidomethyl]-propyl Ester (19b)

Yield 52%, white solid; $^1$H NMR (CDCl$_3$) δ 7.09–7.28 (m, 4H, Ar), 6.85 (m, 3H, Ar), 6.54 (m, 1H, NH), 4.58 (s, 2H, CH$_2$COOH), 4.46 (bs, 2H, NHCH$_2$Ar), 4.12 (ddd of AB, 1H, CH$_2$OC=O), 3.78 (s, 3H, OCH$_3$), 3.7–3.85 (m, 2H, CH$_2$OC=O and CHCH$_2$NHC=S), 3.26 (m, 1H, CHCH$_2$NHC=S), 2.58 (m, 2H, CH$_2$Ph), 2.32 (m, 1H, CHCH$_2$Ph), 1.28 (s, 9H, ArC(CH$_3$)$_3$), 1.22 (s, 9H, CO(CH$_3$)$_3$).

Example 57

Succinic Acid Monobenzyl Ester (20)

A solution of benzyl alcohol (0.52 mL, 5 mmol) in THF (20 mL) was treated with NaH (60%, 0.2 g, 5 mmol) and succinic anhydride (0.502 g, 5 mmol) and refluxed for 4 h. After cooling to room temperature, the reaction mixture was diluted with H$_2$O and extracted with EtOAc several times. The combined organic layer was washed H$_2$O and brine, dried over MgSO$_4$ and concentrated in vacuo. The residue was purified by flash column chromatography over silica gel using EtOAc:Hex (1:1) as eluant to give 20 as white solid (0.866 g, 57%).

$^1$H NMR (CDCl$_3$) δ 7.38 (s, 5H, phenyl), 5.15 (s, 2H, PhCH$_2$), 2.71 (m, 4H, COCH$_2$CH$_2$CO).

Example 58

Succinic Acid Benzyl Ester 4-(Benzyloxycarbonylamino-methyl)-2-methoxy-phenyl Ester (21)

A solution of 10 (0.866 g, 2.85 mmol) in CH$_2$Cl$_2$ (10 mL) was treated with 14 (2.85 mmol), dicyclohexylcarbodiimide (4.2 mmol) and 4-dimethylaminopyridine (0.42 mmol) successively and stirred for 24 h at room temperature. The reaction mixture was diluted with diethyl ether, precipitated solid was filtered and the filtrate was concentrated in vacuo. The residue was purified by flash column chromatography over silica gel using EtOAc:Hex (2:1) as eluant to give 21 as white solid (1.15 g, 85%).

$^1$H NMR (CDCl$_3$) δ 7.30–7.36 (m, 10H, 2×phenyl), 6.86 (m, 3H, Ar), 5.14 (d, 4H, PhCH$_2$), 4.34 (d, 2H, CH$_2$NH), 3.75 (s, 3H, ArOCH$_3$), 2.93 (t, 2H, COCH$_2$CH$_2$CO), 2.79 (t, 2H, COCH$_2$CH$_2$CO).

Example 59

Succinic Acid Mono-(4-aminomethyl-2-methoxy-phenyl) Ester (22)

This compound was prepared from 11 by following the procedure for the synthesis of 17.

Yield 99%, yellow solid; $^1$H NMR (DMSO) δ 8.24 (t, 1H, COOH), 6.75 (m, 3H, Ar), 4.17 (d, 2H, CH$_2$NH), 3.73 (s, 3H, ArOCH$_3$), 2.44 (t, 2H, COCH$_2$CH$_2$CO), 2.34 (t, 2H, COCH$_2$CH$_2$CO).

General Synthesis for the Synthesis of 23

These compounds were prepared from 18 and 22 by following the procedure for the synthesis of 19.

Example 60

Succinic Acid Mono-(4-{3-[3-(3,4-dimethyl-phenyl)-2-(2,2-dimethyl-propionyloxymethyl)-propyl]-thioureidomethyl}-2-methoxy-phenyl) Ester (23a)

Yield 17%, white solid; $^1$H NMR (CDCl$_3$) δ 6.9–7.2 (m, 4H, Ar), 6.8 (m, 3H, Ar), 6.34 (m, 1H, NH), 4.56 (d, 2H, NHCH$_2$Ar), 4.04 (m, 1H, CH$_2$OC=O), 3.84 (s, 3H, OCH$_3$), 3.6–3.85 (m, 2H, CH$_2$)C=O and CHCH$_2$NHC=S), 3.27 (m, 1H, CHCH$_2$NHC=S), 2.65 (m, 2H, CH$_2$Ph), 2.50 (s, 4H, COCH$_2$CH$_2$CO) 2.18–2.29 (m, 7H, 2×CH$_3$ and CHCH$_2$Ph), 1.24 (s, 9H, CO(CH$_3$)$_3$).

Example 61

Succinic Acid Mono-(4-{3-[3-(4-t-butyl-phenyl)-2-(2,2-dimethylpropionyloxymethyl)-propyl]-thioureidomethyl}-2-methoxy-phenyl) Ester (23b)

Yield 9%, white solid; $^1$H NMR (CDCl$_3$) δ 7.07–7.32 (m, 4H, Ar), 6.82 (m, 3H, Ar), 6.59 (m, 1H, NH), 4.87 (m, 3H, NHCH$_2$Ar and CH$_2$OC=O), 4.12 (ddd of AB, 1H, CH$_2$OC=O), 3.85 (s, 3H, OCH$_3$ 3.7–3.89 (m, 2H, CH$_2$OC=O and CHCH$_2$NHC=S), 3.41 (m, 1H, CHCH$_2$NHC=S), 2.58 (m, 2H, CH$_2$Ph), 2.39 (t, 4H, COCH$_2$CH$_2$CO) 2.32 (m, 1H, CHCH$_2$Ph), 1.28 (s, 9H, ArC(CH$_3$)$_3$), 1.21 (s, 9H, CO(CH$_3$)$_3$).

General Procedure for the Synthesis of 25

A mixture of 24 (1.15 mmol) and homovanillic pentafluorophenyl ester (0.4 g, 1.15 mmol) in EtOAc (5 mL) was treated with Lindlar's catalyst and hydrogenated under a balloon of hydrogen for 7 h. The reaction mixture was filtered and the filtrate was concentrated in vacuo. The residue was purified by flash column chromatography over silica gel using EtOAc:Hex (1:2) as eluant to give 25.

Example 62

2,2-Dimethyl-propionic Acid 3-(3,4-Dimethyl-phenyl)-2-{[2-(4-hydroxy-3-methoxy-phenyl)-acetylamino]-methyl}-propyl Ester (25a)

Yield 37%, oil; $^1$H NMR (CDCl$_3$) δ 6.68–7.02 (m, 6H), 5.96 (bs, 1H, NH), 4.00 (m, 1H, CH$_2$OCO), 3.87 (s, 3H, OCH$_3$), 3.80 (m, 1H, CH$_2$OCO), 3.46 (s, 2H, COCH$_2$Ar), 3.32 (m, 1H, CH$_2$NH), 3.13 (m, 1H, CH$_2$NH), 2.50 (d, 2H, CH$_2$Ph), 2.20 (m, 7H, 2×CH$_3$ and CH), 1.20 (s, 9H, CO(CH$_3$)$_3$).

Example 63

2,2-Dimethyl-propionic Acid 3-(4-t-Butyl-phenyl)-2-{[2-(4-hydroxy-3-methoxy-phenyl)-acetylamino]-methyl}-propyl Ester (25b)

Yield 70%, oil; $^1$H NMR (CDCl$_3$) δ 7.28–7.31 (d, 2H), 7.03–7.05 (d, 2H), 6.89 (d, 1H, Ar), 6.80 (d, Ar), 6.72 (d, 1H, Ar), 5.8 (bs, 1H, NH), 4.02 (m, 1H, CH$_2$OCO), 3.89 (s, 3H, OCH$_3$), 3.83 (m, 1H, CH$_2$OCO), 3.49 (s, 2H, COCH$_2$Ar), 3.34 (m, 1H, CH$_2$NH), 3.12 (m, 1H, CH$_2$NH), 2.56 (d, 2H, CH$_2$Ph), 2.13 (m, 1H, CH), 1.31 (s, 9H, C(CH$_3$)$_3$ ), 1.22 (s, 9H, CO(CH$_3$)$_3$).

General Procedure for the Synthesis of 26

A mixture of (0.33 mmol), 40% KOH (0.24 mL), 40% tetrabutylammonium hydroxide (0.02 mL, 0.03 mmol) and 1,2-dibromoethane (0.96 mL) was heated at 50° C. for 12 h. The reaction mixture was diluted with $CH_2Cl_2$, washed with $H_2O$ and brine, dried over $MgSO_4$ and concentrated in vacuo. The residue was purified by flash column chromatography over silica gel using EtOAc:Hex (1:2) as eluant to give 26.

Example 64

2,2-Dimethyl-propionic Acid 2-({2-[4-(2-Bromoethoxy)-3-methoxyphenyl]acetylamino}methyl)-3-(3,4-dimethylphenyl)propyl Ester (26a)

Yield: 68%; $^1H$ NMR ($CDCl_3$) δ 6.74–7.03 (m, 6H), 5.75 (bs, 1H, NH), 4.32 (t, 2H, $OCH_2$), 4.01 (m, 1H, $CH_2OCO$), 3.86 (s, 3H, $OCH_3$), 3.82 (m, 1H, $CH_2OCO$), 3.64 (t, 2H, $CH_2Br$), 3.47 (s, 2H, $COCH_2Ar$), 3.31 (m, 1H, $CH_2NH$), 3.10 (m, 1H, $CH_2NH$), 2.50 )d, 2H, $CH_2Ph$), 2.20 (m, 7H, 2×CH3 and CH), 1.21 (s, 9H, $CO(CH_3)_3$).

Example 65

2,2-Dimethyl-propionic Acid 2-({2-[4-(2-Bromoethoxy)-3-methoxyphenyl]acetylamino}methyl)-3-(4-t-butylphenyl)propyl Ester (26b)

Yield 92%; $^1H$ NMR ($CDCl_3$) δ 7.26–7.30 (d, 2H), 7.01–7.04 (d, 2H), 6.74–6.89 (m, 3H, Ar), 5.8 (bs, 1H, NH), 4.3 (t, 2H, $OCH_2$), 4.01(m, 1H, $CH_2OCO$), 3.86 (s, 3H, $OCH_3$), 3.82 (m, 1H, $CH_2OCO$), 3.64 (t, 2H, $CH_2Br$), 3.47 (s, 2H, $COCH_2Ar$), 3.31 (m, 1H, $CH_2NH$), 3.10 (m, 1H, $CH_2NH$), 2.5 (d, 2H, $CH_2Ph$), 2.12 (m, 1H, CH), 1.30 (s, 9H, $C(CH_3)_3$), 1.22 (s, 9H, $CO(CH_3)_3$).

General Procedure for the Synthesis of 27

A solution of 26 (0.22 mmol) in DMF (2 mL) was treated with sodium azide (0.044 g, 0.67 mmol) and heated at 100° C. for 8 h. The reaction mixture was diluted with $H_2O$ and extracted with EtOAc. The combined organic layer was washed with $H_2O$ and brine, dried over $MgSO_4$ and concentrated in vacuo. The residue was purified by flash column chromatography over silica gel using EtOAc:Hex (1:1) as eluant to give 27.

Example 66

2,2-Dimethyl-propionic Acid 2-({2-[4-(2-Azidoethoxy)-3-methoxyphenyl]acetylamino}methyl)-3-(3,4-dimethylphenyl)propyl Ester (27a)

Yield 98%; $^1H$ NMR ($CDCl_3$) δ 6.74–7.03 (m, 6H), 5.74 (bs, 1H, NH), 4.19 (t, 2H, $OCH_2$), 4.01 (m, 1H, $CH_2OCO$), 3.85 (s, 3H, $OCH_3$), 3.82 (m, 1H, $CH_2OCO$), 3.62 (t, 2H, $CH_2N_3$), 3.48 (s, 2H, $COCH_2Ar$), 3.29 (m, 1H, $CH_2NH$), 3.10 (mn, 1H, $CH_2NH$), 2.50 (d, 2H, $CH_2Ph$), 2.04–2.26 (m, 7H, 2×$CH_3$ and CH), 1.21 (s, 9H, $CO(CH_3)_3$).

Example 67

2,2-Dimethyl Propionic Acid 2-({2-[4-(2-Azidoethoxy)-3-methoxyphenyl]acetylamino}methyl)-3-(4-t-butylphenyl)propyl Ester (27b)

Yield 81%; $^1H$ NMR ($CDCl_3$) δ 7.26–7.30 (d, 2H), 7.01–7.04 (d, 2H), 6.75–6.91 (m, 3H, Ar), 5.76 (bs, 1H, NH), 4.17 (t, 2H, $OCH_2$), 4.00 (m, 1H, $CH_2OCO$), 3.85 (s, 3H, $OCH_3$), 3.82 (m, 1H, $CH_2OCO$), 3.63 (t, 2H, $CH_2N_3$), 3.48 (s, 2H, $COCH_2Ar$), 3.31 (m, 1H, $CH_2NH$), 3.06 (m, 1H, $CH_2NH$), 2.54 (d, 2H, $CH_2Ph$), 2.12 (m, 1H, CH), 1.29 (s, 9H, $C(CH_3)_3$), 1.20 (s, 9H, $CO(CH_3)_3$).

General Procedure for the Synthesis of 28

A solution of 27 (0.05 mmol) in MeOH (5 mL) was treated with 10% palladium on carbon (0.02 g) and hydrogenated under a balloon of hydrogen for 3 h. The reaction mixture was filtrated and the filtrate was concentrated in vacuo. The residue was purified by flash column chromatography over silica gel using $CHCl_3$:MeOH: $NH_4OH$ (9:1:0.1) as eluant to give 28.

Example 68

2,2-Dimethyl Propionic Acid 2-({2-[4-(2-Aminoethoxy)-3-methoxyphenyl]acetylamino}methyl)-3-(3,4-dimethylphenyl)propyl Ester (28a)

Yield 83%, white solid; $^1H$ NMR ($CDCl_3$) δ 6.73–7.23 (m, 6H), 5.73 (bs, 1H, NH), 4.13 (m, 3H, $OCH_2$ and $CH_2OCO$), 3.85 (s, 3H, $OCH_3$), 3.82 (m, 1H, $CH_2OCO$), 3.5 (m, 2H, $COCH_2Ar$), 3.23 (m, 2H, $CH_2NH$ and $CH_2NH_2$), 3.09 (m, 2H, $CH_2NH$ and $CH_2NH_2$), 2.50 (d, 2H, $CH_2Ph$), 2.04–2.26 (m, 7H, 2×$CH_3$ and CH), 1.20 (s, 9H, $CO(CH_3)_3$).

Example 69

2,2-Dimethyl Propionic Acid 2-({2-[4-(2-Aminoethoxy)-3-methoxyphenyl]acetyl amino}methyl)-3-(4-t-butylphenyl)propyl Ester (28b)

Yield 99%, white solid; $^1H$ NMR ($CDCl_3$) δ 7.26–7.29 (m, 2H), 7.01–7.04(d, 2H), 6.76–6.89 (m, 3H, Ar), 5.84 (bs, 1H, NH), 4.05 (m, 1H, $CH_2OCO$), 3.85 (m, 3H, $OCH_3$), 3.72 (m, 3H, $CH_2OCO$ and $OCH_2$), 3.47 (s, 2H, $COCH_2Ar$), 3.30 (m, 1H, $CH_2NH$), 3.10 (m, 1H, $CH_2NH$), 2.75 (bs, 2H, $CH_2NH_2$) 2.52 (d, 2H, $CH_2Ph$), 2.12 (m, 1H, CH), 1.29 (s, 9H, $C(CH_3)_3$), 1.20 (s, 9H, $CO(CH_3)_3$).

Example 70

(4-Hydroxy-3-methoxybenzyl)carbamic Acid t-butyl Ester (30)

A mixture of 4-hydroxy-3-methoxy benzylamine (29, 0.5 g, 2.64 mmol) and $NEt_3$ (0.054 g, 5.29 rmnol) in $H_2O$ (10 mL) was treated dropwise with a solution of di-t-butyl-dicarbonate (1.15 g, 5.29 mmol) in dioxane (1.5 mL) for 20 min. After stimrng for 24 h at room temperature, the reaction mixture was extracted with $CH_2Cl_2$ several times. The combined organic layer was dried over $MgSO_4$ and concentrated in vacuo. The residue was purified by flash column chromatography over silica gel using EtOAc:Hex (1:1) as eluant to give 30 as oil (0.663 g, 99%).

$^1H$ NMR ($CDCl_3$) δ 6.74–7.00 (m, 3H, Ar), 5.65 (s, 1H, OH), 4.79 (bs, 1H, NH), 4.23 (d, 2H, $NHCH_2$) 3.87 (s, 3H, $OCH_3$), 1.43 (s, 9H, $O(CH_3)_3$).

Example 71

[4-(2-Bromo-ethoxy)-3-methoxy-benzyl]-carbamic Acid t-Butyl Ester (31)

This compound was prepared from 30 by following the same procedure for the synthesis of 26. (EtOAc:Hex=1:3), yield 84%.

$^1$H NMR (CDCl$_3$) δ 6.78–6.89 (m, 3H, Ar), 4.81 (bs, 1H, NH), 4.29–4.33 (t, 2H, OCH$_2$), 4.24 (d, 2H, NHCH$_2$), 3.90 (s, 3H, OCH$_3$), 3.65 (t, 2H, CH$_2$Br), 1.46 (s, 9H, O(CH$_3$)$_3$).

Example 72

(4-(2-Azido-ethoxy)-3-methoxy-benzyl]-carbamic Acid t-Butyl Ester (32)

This compound was prepared from 21 by following the same procedure for the synthesis of 27. (EtOAc:Hex=1:3), yield 98%, yellow solid.

$^1$H NMR (CDCl$_3$) δ 6.78–6.87 (m, 3H, Ar), 4.83 (bs, 1H, NH), 4.24 (d, 2H, OCH$_2$), 4.15 (t, 2H, NHCH$_2$), 3.80 (s, 3H, OCH$_3$), 3.62 (t, 2H, CH$_2$N$_3$), 1.46 (s, 9H, (CH$_3$)$_3$).

Example 73

(4-(2-Azidoethoxy)-3-methoxy-benzylamine Trifluoroacetate (33)

A solution of 32 (0.103 g, 0.32 mmol) in CH$_2$Cl$_2$ (1 mL) was treated with trifluoroacetic acid and heated at 100° C. for 1 hr. The reaction mixture was concentrated in vacuo. The residue was diluted with toluene and concentrated in vacuo several times to give 33 as brown solid (0.115 g, 100%).

$^1$H NMR (DMSO-d$_6$) δ 6.99–7.10 (m, 3H, Ar), 4.12 (t, 2H, OCH$_2$), 3.93 (s, 2H, ArCH$_2$), 3.76 (s, 3H, OCH$_3$), 3.62 (m, 2H, CH$_2$N$_3$).

Example 74

1-(2-Azidoethoxy)-4-isothiocyanatomethyl-2-methoxy Benzene (34)

A solution of 33 (0.115 g, 0.33 mmol) in DMF (1.5 mL) was treated with NEt$_3$ (0.037 g, 0.36 mmol) and stirred for 1 h. The mixture was treated with 1,1-thiocarbonyl di-2-(1H)-pyridone (0.084 g, 0.33 mmol) and stirred for 2.5 h at room temperature. The mixture was diluted with H$_2$O and extracted with diethyl ether several times. The combined organic layer was washed with H$_2$O and bnine, dried over MgSO$_4$ and concentrated in vacuo. The residue was purified by flash column chromatography over silica gel using EtOAc:Hex (1:2) as eluant to give 34 as oil (0.065 g, 74%)

$^1$H NMR (CDCl$_3$) δ 6.75–6.91 (m, 3H, Ar), 4.65 (s, 2H, CH$_2$N=C=S), 4.20 (t, 2H, OCH$_2$), 3.90 (s, 3H, OCH$_3$), 3.62 (t, 211, CH$_2$N$_3$)

General Procedure for the Synthesis of 35

A solution of 6 (0.27 mmol) in EtOH (5 mL) was treated with Lindler's catalyst (0.042 mg) and hydrogenated under a balloon of hydrogen for 2 h. The reaction mixture was Z 10 filtered and the filtrate was concentrated. The residue was dissolved in CH$_2$Cl$_2$ (5 mL) and treated with 34 (0.27 mmol). After stirring for 15 h at room temperature, the reaction mixture was concentrated in vacuo. The residue was purified by flash column chromatography over silica gel using EtOAc:Hex (1:10) as eluant to give 35.

Example 75

2,2-Dimethyl Propionic Acid 2-{3-[4-(2-Azidoethoxy)-3-methoxybenzyl]thioureido Methyl}-3-(3,4-dimethylphenyl)propyl ester (35a)

Yield 39%; $^1$H NMR (CDCl$_3$) δ 6.81–7.04 (m, 6H), 6.25 (m, 1H, NH), 6.02 (bs, 1H, NH), 4.41 (bs, 2H, NHCH$_2$Ar), 4.14–4.17 (m, 3H, CH$_2$OCO and OCH$_2$), 3.85 (s, 3H, OCH$_3$), 3.76–3.85 (m, 2H, CH$_2$OCO and CHCH$_2$NHC=S), 3.60–3.63 (t, 2H, CH$_2$N$_3$ ), 3.21–3.28 (m, 1H, CHCH$_2$NC=S), 2.47–2.66 (m, 2H, CH$_2$Ph), 2.20–2.26 (m, 7H, 2×CH$_3$ and CH), 1H, (s, 9H, CO(CH$_3$)$_3$).

Example 76

2,2-Dimethyl Propionic Acid 2-{3-[4-(2-Azidoethoxy)-3-methoxybenzyl]thioureido Methyl}-3-(4-t-butylphenyl)propyl Ester (35b)

Yield 60%; $^1$H NMR (CDCl$_3$) δ 7.3 (d, 2H), 7.08 (d, 2H), 6.9 (m, 3H, Ar), 6.28 (m, 1H, NH), 6.10 (bs, 1H, NH), 4.43 (bs, 2H, NHCH$_2$Ar), 4.2 (m, 3H, CH$_2$OCO and OCH$_2$) 3.85 (s, 3H, OCH$_3$), 3.74–3.95 (m, 2H, CH$_2$OCO and CHCH$_2$NHC=S), 3.60–3.63 (t, 2H, CH$_2$N$_3$), 30 3.26 (m, 1H, CHCH$_2$NHC=S), 2.6 (m, 2H, CH$_2$Ph), 2.30 (m, 1H, CH), 1.29 (s, 9H, CO(CH$_3$)$_3$).

General Synthesis for the Synthesis of 36

A solution of 35 (0.068 g, 0.13 mmol) in THF (2 mL) was treated with triphenylphosphine (0.067 g, 0.25 numol) and H$_2$O (4.5 mg, 0.25 mmol) and stirred for 24 h at room temperature. The reaction mixture was concentrated in vacuo and the residue was purified by flash column chromatography over silica gel using CHCl$_3$:MeOH:NH$_4$OH (9:1:0.1) as eluant to give 36.

Example 77

2,2-Dimethyl Propionic Acid 2-{3-[4-(2-Aminoethoxy)-3-methoxybenzyl]thioureido Methyl}-3-(3,4-dimethylphenyl)propyl Ester (36a)

Yield 49%; $^1$H NMR (CDCl$_3$) δ 6.77–7.04 (m, 6H), 6.47 (bs, 2H, NH), 4.43 (bs, 2H, NHCH$_2$Ar), 4.18 (ddd of AB, 1H, CH$_2$OCO), 3.98 (t, 2H, OCH$_2$), 3.81 (s, 3H, OCH$_3$), 3.71–3.77 (m, 2H, CH$_2$OCO and CHCH$_2$NHC=S), 3.06 (t, 2H, CH$_2$NH$_2$), 2.48–2.68 (m, 2H, CH$_2$Ph), 2.20 (m, 7H, 2×CH$_3$ and CH), 1.23 (s, 9H, CO(CH$_3$)$_3$).

Example 78

2,2-Dimethyl Propionic Acid 2-{3-[4-(2-Aminoethoxy)-3-methoxybenzyl]thioureido Methyl}-3-(4-t-butylphenyl)propyl Ester (36b)

Yield 99%; $^1$H NMR (CDCl$_3$) δ 7.28–7.47 (m, 2H), 7.2 (d, 2H), 6.8–7.0 (m, 3H, Ar), 6.4 (bs, 1H, NH), 4.44 (bs, 2H, NHCH$_2$Ar), 4.18 (m, 1H, CH$_2$OCO), 3.82 (t, 2H, OCH$_2$), 3.78 (s, 3H, OCH$_3$), 3.66–3.82 (m, 2H, CH$_2$OCO and CHCH$_2$NHC=S), 3.09 (t, 2H, CH$_2$NH$_2$), 2.48–2.68 (m, 2H, CH$_2$Ph), 2.20 (m, 1H, CH), 1.28 (s, 9H, C(CH$_3$)$_3$), 1.22(s, 9H, CO(CH$_3$)$_3$).

Experimental Example 1

Receptor Binding Affinity and CAP-activated Channel Assay

The CAP-like activity of the target compounds was measured by an in vitro receptor binding assay and a CAP-activated single channel activation assay. In the receptor binding assay, the compounds were evaluated for their ability to displace bound [$^3$H]RTX from the receptor. The results are expressed in terms of K$_i$ values (mean±SEM, 3 experiments) which represent the concentration of the non-radioactive ligand that displaces half of the bound labeled RTX. In the CAP-activated single channel activation assay, the increase of inward current resulting from the nonselective cation influx was measured following the extracellular application of the compounds to cultured neonatal rat dorsal root ganglion (DRG) neurons. The activities of the compounds are expressed in terms of the relative difference in ion conductance compared to CAP as a control.

Methods

1. [$^3$H]Resiniferatoxin Binding Assay.

[$^3$H]RTX (37 Ci/mmol) was synthesized by the Chemical Synthesis and Analysis Laboratory, NCI-FCRDC. Nonradioactive RTX and capsazepine were purchased from LC Laboratories (Woburn, Mass.).

Inhibition of [$^3$H]RTX binding in the presence of competing ligands was determined on membrane preparations from rat spinal cord. Membrane preparations were prepared as described (Methods in Neurosciences Vol 8, pp 368–380). Briefly, animals were euthanized under general anesthesia and the entire spinal cord was removed aseptically. Samples were disrupted with the aid of an Omni 2000 tissue homogenizer in ice-cold 10 mM HEPES, pH 7.4, containing 5 mM KCl, 5.8 mM NaCl, 2 mM MgCl$_2$, 0.75 mM CaCl$_2$, 12 mM D-glucose, and 137 mM sucrose ("Buffer A"). Homogenates were centrifuged at 1,000×g for 10 min at 4° C.; pellets were resuspended in Buffer A and recentrifuged at 35,000×g for 40 min at 4° C. The pellets from the second centrifugation were resuspended in the same buffer at an approximate protein concentration of 2 mg/ml, quick frozen on dry ice as small aliquots, and stored at −70° C. until assayed.

Experiments were designed to assess inhibition of specific [$^3$H]RTX binding to membranes by non-radioactive compounds. [$^3$H]RTX (100 pM) was incubated in the presence of competing ligand in a total volume of 300:1 with 100 g membrane protein for 60 min at 37° C. in Buffer A supplemented with 0.25 mg/ml bovine serum albumin (type V, Sigma). The bovine serum albumin was included to reduce nonspecific adsorption of RTX to surfaces. At the end of the incubation, tubes were chilled on ice and 100 μg of α$_1$-acid glycoprotein (Sigma) in a 50:1 volume was added to each tube to reduced nonspecific binding. Bound and free [$^3$H]RTX were then separated by pelleting the membranes by centrifugation at 10,000×g for 15 min at 4° C. The tips of the tubes containing the pellets were cut off, and the bound radioactivity was determined by scintillation counting. Nonspecific binding was determined in the presence of 1 mM non-radioactive RTX. Measurements of binding were determined in triplicate in each experiment, and each experiment was repeated at least two times. In each experiment, competition curves were determined typically using 5–6 concentrations of competing ligand.

Binding was expressed as fmol/mg protein. Protein concentration was measured using the Bio-Rad protein assay according to the manufacturer's protocol (Bio-Rad Laboratories, Calif.). Samples were equilibrated in scintillation fluid for 10 hrs before scintillation counting began and each sample was counted for 5 min. Binding data were analyzed by fitting to the following equation:

$$B=((L_H+L_C*K_d/K_f)^{n-1})/(K_d^n+(L_H+L_C*K_d/K_f)^n)/(L_H^{n-1}/(K_d^n+L_H^n))$$

where $L_C$ is the concentration of the non-radioactive ligand and $K_f$ is the concentration of the free non-radioactive ligand at which it occupies half of the binding sites. B represents specifically bound [$^3$H]RTX, Bmax is the receptor density, $L_H$ is the concentration of free [$^3$H]RTX, $K_d$ is the concentration of [$^3$H]RTX at which half of the receptors are occupied and n is the cooperativity index referred to as the Hill coefficient.

2. Capsaicin-activated Single Channel Assay.

Cell Preparation. Cultured DRG neurons were prepared as described previously (J. Neuroscience 16, 1659–1667, (1996)). Briefly, DRGs were dissected from all levels of lower cervical, thoracic and lumbar spinal cord of 1 or 2 day old neonatal rats. DRGs were collected in cold culture medium (4° C.) containing DMEM/F-12 mixture (Gibco, Grand Island, N.Y.), fetal bovine serum (10%, Gibco), 1 mM sodium pyruvate, 25 ng/ml nerve growth factor (Sigma, St. Louis, Mo.), and 100 units/ml of penicillin/streptomycin (Sigma). Ganglia were washed 3 times with DMEM/F-12 medium and incubated for 30 minutes in the DMEM/F-12 medium containing 1 mg/ml collagenase (Type II, Worthington Biomedical, Freehold, N.J.). The ganglia were then washed 3 times with Mg$^{2+}$- and Ca$^{2+}$-free Hank's solution and incubated with gentle shaking in the warm (37° C.) Hank's solution containing 2.5 mg/ml trypsin (Gibco). The solution was centrifuged at 1,000 rpm for 10 min, and the pellet was washed 2 or 3 times with the culture medium to inhibit the enzyme. The pellet was suspended in the culture medium and gently triturated with a Pasteur pipette. The suspension was plated on round glass coverslips (Fisher, Pittsburgh, Pa.) placed in small Petri dishes. The glass coverslips were treated overnight with poly-L-lysine (Sigma) and dried before use. Cells were incubated at 37° C. in 95% air/5% CO$_2$ gas mixture. Cells were used 2–4 days after plating.

Current recording. Borosilicate glass pipettes (Narishige Scientific Instrument Lab., Tokyo) were pulled and coated with Sylgard (Dow Corning Co., Midland, Mich.). Tip resistances were about 2 and 5 Mohms for whole-cell and single-channel current recordings, respectively. After gigaseals were formed with the glass pipettes, cell-attached and inside-out patch configurations were used to study single-channel currents as described by Hamill et al. A salt bridge (1% agar in 300 mM KCl) immersed in bath and an Ag/AgCl reference electrode in pipette solution was used to minimize changes in junctional potentials. Junctional potentials were canceled before gigaseals were formed. For whole-cell recording, the cell membrane under a glass pipette was ruptured by a gentle suction. After forming a whole-cell, capacitative transient was canceled. Single-channel currents were recorded using a patch-clamp amplifier (Axopatch 200A, Axon Instruments, Foster City, Calif.) and filtered at 5 KHz with an 8-pole, low-pass Bessel filter. Data were digitized at 37 KHz with a digital data recorder (VR-10B, Instrutech, Great Neck, N.Y.) and stored on videotapes for later analysis. For chart recording, output of amplifier was filtered at 500 Hz (Frequency Device, Havenhill, Mass.) and fed into a thermal array chart recorder (TA-240, Gould Instrument System, Valley View, Ohio). The digitized data stored on videotapes were imported to a personal computer (IBM pentium-compatible) for computer analysis of single-channel currents.

Channel open probability ($P_O$), amplitude and mean open time of single-channel currents were obtained using the pCLAMP software (Version 6.02, Axon Instruments). $P_O$ of single channels was obtained from the ratio of the areas under the curves representing open events divided by the sum of the areas under the curves representing open and closed events. The half-amplitude algorithm in FETCHAN (Axon Instruments) was used for the threshold amplitude for detecting open events. Channel activity (NP$_O$) was calculated as a product of the number of channel (N) in the patch and $P_O$. NPo or $P_O$ was collected only from patches that contained less than 5 functional CAP-activated channels.

Solutions. Solutions in bath and pipette for single-channel recordings contained (in mM) 140 Na$^+$, 2 Mg$^{2+}$, 144 Cl$^-$, 5

EGTA, and 10 HEPES at pH 7.2. For whole cell, pipette solution contained (in mM) 140 $K^+$, 2 $Mg^{2+}$, 144 $Cl^-$, 5 EGTA, 10 HEPES, and 4 ATP at pH 7.2. The control perfusion solution for whole-cell recording contained (in mM) 140 $Na^+$, 5 $K^+$, 2 $Mg^+$, 1 $Ca^+$, 151 $Cl^-$, and 10 HEPES. The synthesized compounds were dissolved and stored in 100% ethanol to make 10 mM stock solutions. All other reagents used in cell-culture or in electrophysiological experiments were purchased from Signa. All values were expressed as means±S.E.

Results

The results are presented in Table 1 and can be summarized as follows: (1) all the compounds tested, except 7b-Ia, showed stronger agonist activity and receptor binding affinity than CAP; (2) the thiourea analogue 7a-I ($K_i$=65.6 nM) exhibited more potent agonist activity than the CAP-related amide analogue ($K_i$=404 mM) reported in our earlier study; (3) the ester group in $R_1$, which was designed to mimic the $C_3$-carbonyl of RTX, appears to be important for potent agonist activity relative to the benzyl ether analogues in $R_1$ [compare 7a-V ($K_i$=31.2 nM) and 7c-V ($K_i$=148.7 nM) with 9a ($K_i$=148 nM) and 9c ($K_i$=659 nM)] suggesting an important role for the carbonyl moiety in hydrogen-bonding to the receptor; (4) the pivaloyl group at $R_1$ and the 4-t-butylbenzyl group at $R_2$ proved to be effective hydrophobic groups resulting in optimal agonist activity for compounds 7b-I and 7d-I ($K_i$=19 nM and 10.8 nM, respectively) which are ca. 280 and 490 times more potent than CAP; and (5) binding of thiourea to the receptor appears to be quite stereospecific as the two optically active enantiomers of 7a-I showed substantial differences in receptor binding affinity relative to the racemate [compare 7a-I ($K_i$=65.6 nM) with (R)-7a-I ($K_i$=18.43 nM) and (S)-7a-I ($K_i$=74 nM)].

TABLE 1

Binding Affinities and Channel Activations

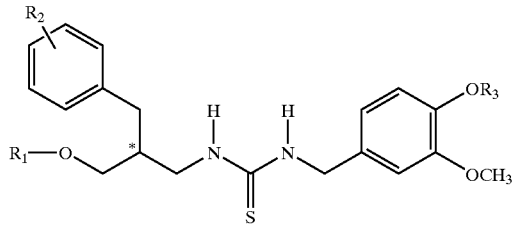

| | $R_1$ | $R_2$ | $R_3$ | Affinities (nM) | Activations[a] |
|---|---|---|---|---|---|
| CAP | | | | 5,310 (±370) | |
| RTX | | | | 0.023 | |
| Amide | $(CH_3)_3CCO$ | H | H | 404 (±37) | ++ |
| 7a-I | $(CH_3)_3CCO$ | H | H | 65.6 (±30.5) | +++ |
| (R)-7a-I | $(CH_3)_3CCO$ | H | H | 18.43 (±5.1) | +++ |
| 10 | $(CH_3)_3CCO$ | H | $CH_2OCH_3$ | 146.2 (±48) | ++ |
| (S)-7a-I | $(CH_3)_3CCO$ | H | H | 74 (±16) | ++ |
| 7a-II | $(CH_3)_2CHCO$ | H | H | 132.9 (±75) | +++ |
| 7a-III | $CH_3(CH_2)_4CO$ | H | H | 632.3 (±48) | ++ |
| 7a-IV | $CH_3(CH_2)_{16}CO$ | H | H | 1,873 (±351) | + |
| 7a-V | PhCO | H | H | 31.2 (±9) | ++ |
| 9a | $PhCH_2$ | H | H | 148 (±11) | ++ |
| 7b-I | $(CH_3)_3CCO$ | 3,4-diMe | H | 19 (±4.3) | ++ |
| 7b-Ia | $(CH_3)_3CCO$ | 3,4-diMe | $CH_2OCH_3$ | 876 (±65) | W |
| 7b-V | PhCO | 3,4-diMe | H | 409 (±178) | ++ |
| 7b-VI | (3,4-Me)PhCO | 3,4-diMe | H | 183.5 (±69) | +++ |
| 7c-I | $(CH_3)_3CCO$ | 4-Cl | H | 54.4 (±16) | ++ |
| 7c-V | PhCO | 4-Cl | H | 148.7 (±11) | ++ |

TABLE 1-continued

Binding Affinities and Channel Activations

| | $R_1$ | $R_2$ | $R_3$ | Affinities (nM) | Activations[a] |
|---|---|---|---|---|---|
| 9c | $PhCH_2$ | 4-Cl | H | 659 (±286) | ++ |
| 7d-I | $(CH_3)_3CCO$ | 4-t-Bu | H | 10.8 (±4) | ++ |
| 7d-V | PhCO | 4-t-Bu | H | 60.2 (±10) | ++ |

[a] + = CAP, ++ = 10 CAP, +++ = 100 CAP

Experimental Example 2

Analgesic and Antiinflammatory Activity

The analgesic activity of some of the most potent capsaicin agonists, selected from the receptor binding and single channel assays, was evaluated in the PBQ-induced writhing assay and the results are shown in Table 2. As expected, two of the most potent compounds based on the in vitro assay, 7d-I and 7b-I, exhibited excellent analgesic activities with $ED_{50}$ of 0.5 and 1 µg/kg, respectively. Such values make these compound 300 to 600 times more potent than CAP. Both compounds were likewise more potent than olvanil or DA-5018, which are either currently available in the market or undergoing clinical trial as topical analgesics.

In the TPA-induced ear edema assay, even the most potent agonists of the inventive compounds showed weak antiinflammatory activity compared to the strong anti-edema activity of CAP (Table 2). We had originally speculated that the thiourea analogues, with their higher intrinsic potency, might dramatically reduce the TPA-induced ear edema. In this respect, their activity resembles that of olvanil or DA-5018, both of which display weak topical activity in the TPA ear edema assay. Poor bioavailability through transcutaneous penetration may explain in part the weak topical antiinflammatory properties observed with these compounds.

The in vitro and analgesic activities of the compounds of the invention were evaluated by calcium-influx assay and acetic acid-induced writhing test, respectively.

As shown in Table 3, they all exhibited receptor agonistic activities comparable to capsaicin. Among them, aminoethyl analogues relatively displayed potent analgesic activities. Especially compound 28a was proved the most potent one and more potent than DA-5018 which are undergoing clinical trial as analgesic in Korea.

Methods

1. Mouse PBQ-induced Writhing Antinociceptive Assay.

Male ICR mice (weight 25 g) were maintained in a controlled lighting environment (12 h on/12 h off). Animals received an intraperitoneal injection of 0.3 mL of the chemical irritant phenyl-p-quinone (4.5 mg/kg dissolved in saline containing 5% ethanol), and 6 minutes later the number of abdominal constrictions was counted in the subsequent 6 minutes period. Animals (10 animals/group) received the synthesized compounds in 0.2 mL vehicle of ethanol/Tween-80/saline (10/10/80) intraperitoneally 30 min before the injection of phenyl-p-quinone. A reduction in the number of writhes responding to phenyl-p-quinone relative to the number responding in the saline control group was considered to be indicative of an antinociceptive effect. The data are expressed as $ED_{50}$ value to designate a 50% reduction in the number of writhes.

2. Acetic Acid-induced Writhing Test

ICR mice (weight 20 g) were maintained in a controlled lighting environment (12 h on/12 h off) and fasted overnight prior to testing. Animals received an intraperitoneal injection of 0.2 ml of an acetic acid solution (1.2%), and 6 min later the number of abdominal constrictions was counted for a 6-min period. Mice (10 animals/group) were pretreated with drug or vehicle (10 ml/kg, i.p.) 1 hr before the injection of acetic acid. Test compounds were dissolved in ethanol/Tween-80/saline (10/10/80). Antinociceptive activity was expressed as the reduction in the number of abdominal constrictions, i.e. the difference between control animals (vehicle-pretreated mice) and animals pretreated with test compounds.

3. TPA-induced Mouse Ear Edema Assay.

Male ICR mice (25–30 g), 10 animals/group, were treated topically on the right ear with 25 µL acetone or synthesized compound in acetone. Approximately 17 hours later, an identical treatment was applied. One hour later, 25 µL of 0.5 mmol TPA in acetone was applied to the same ear. Five (5) hours following the application of TPA, the animals were sacrificed and ear punches (6 mm diameter) were weighed to the nearest 0.1 mg on an electrobalance. The increased weight of the ear punch is a measure of inflammation (ear edema). Anti-inflanmmatory effects were expressed as percent inhibition of swelling in the compound-treated versus the control group. The percent inhibition is defined by the following equation.

% Inhibition=(C−T)/C×100 wherein C and T refer to increases in ear weight in TPA-treated and TPA+drug-treated groups, respectively.

4. $^{45}Ca$ Uptake Experiments

1) Culture of DRG Neurons

DRG neurons were prepared from neonatal Sprague-Dawley rats by the method as previously described (Wood et al., 1988) with modification. In brief, DRGs of all spinal levels were dissected asceptically and collected. Ganglia were incubated sequentially for 30 min at 37° C. in 200 U/ml collagenase and 2.5 mg/ml trypsin. The digestion was halted by addition of an equal volume of DME/F12 medium supplemented with 10% horse serum. The ganglia were then triturated through a fire-polished Pasteur pipette, filtered through nylon membrane, and spun down. Dissociated cells were plated onto Terasaki plates previously coated with 10 µg/ml poly-D-ornithine at a density of 1500–1700 neurons/well. The cells were then cultured for 3–4 days in DME/F12 medium containing 1.2 g/l sodium bicarbonate, 15 mM HEPES, 50 mg/l gentamycin and 10% horse serum, diluted 1:1 with identical medium conditioned by C6 glioma cells (2 days on a confluent monolayer), in a humidified atmosphere at 37° C. containing 5% $CO_2$. Medium was supplemented with 200 ng/ml nerve growth factor. Cytosine arabinoside (100 µM) was added for the first 2 days to kill dividing nonneuronal cells.

2) Uptake Experiment

Terasaki plates containing DRG neurons grown for 3–4 days were equilibrated with 4 washes of HEPES (10 mM, pH 7.4)-buffered calcium and magnesium-free Hank's balanced salt solution. The solution in each well was removed from the individual wells. Medium (10 µl) containing the test concentration of compound plus 10 µCi/ml $^{45}Ca^{2+}$ was added to each well. The neurons were incubated at room temperature for 10 min, then the Terasaki plates were washed six times in HEPES (10 mM, pH 7.4)-buffered calcium and magnesium-free Hank's balanced salt solution and dried in an oven. 0.3% sodium dodecyl sulfate (10 µl) was then added to dissolve the cells and extract the $^{45}Ca^{2+}$. The contents of each well were transferred to scintillation vials and counted in 3 ml of Aquasol-2 scintillant. Agonistic activities of test compounds were calculated as percent of the maximal response of capsaicin at a concentration of 3 µM and results are given as $EC_{50}\pm SEM$.

Results

TABLE 2

PBQ-induced Writhing test and Ear Edema Assay

|  | Writhing Test $ED_{50}$ (µg/kg) | Relative Potency | Ear Edema Assay $ID_{50}$ (µg/ear) | Relative Potency |
|---|---|---|---|---|
| Capsaicin | 300 | 1 | 3 | 1 |
| RTX | 0.01 | 30,000 | 0.002 | 1,500 |
| Olvanil | 30 | 10 | 30 | 0.1 |
| DA-5018* | 3 | 100 | 200 | 0.015 |
| Indomethacin | 400 | 0.75 |  |  |
| Aspirin | 3,500 | 0.086 |  |  |
| Morphine | 1,000 | 0.3 |  |  |
| 7a-I | 2 | 150 | 25 | 0.12 |
| (R)-7a-I | 8 | 38 |  |  |
| (S)-7a-I | 9 | 33 |  |  |
| 7a-II | 15 | 20 |  |  |
| 7a-III | 5 | 60 |  |  |
| 7a-IV | 20 | 15 |  |  |
| 7a-V | 20 | 15 | 20 | 0.15 |
| 7b-I | 0.5 | 600 | 18 | 0.17 |
| 7b-V | 7 | 43 | 50 | 0.06 |
| 7b-VI | 2 | 150 | 50 | 0.06 |
| 7c-I | 5 | 60 | 22 | 0.14 |
| 7c-V | 12 | 25 | 17 | 0.18 |
| 7d-I | 1 | 300 | 5 | 0.6 |
| 7d-V | 1.5 | 200 | 30 | 0.1 |

*DA-5018

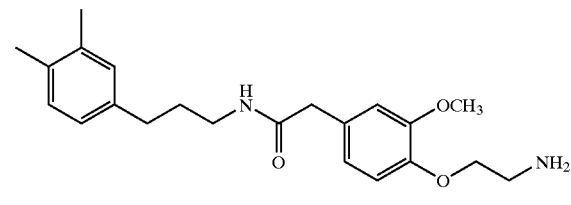

DA-5018
C22H30N2O3

2-[4-(2-aminoethoxy)-3-methoxyphenyl]-N-[3-(3,4-dimethylphenyl)propyl]acetamide

TABLE 3

Calcium Influx Assay and Acetic Acid-Induced Writhing Assay

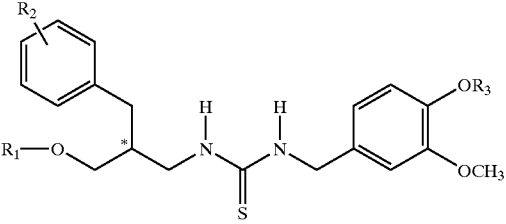

(I-a)

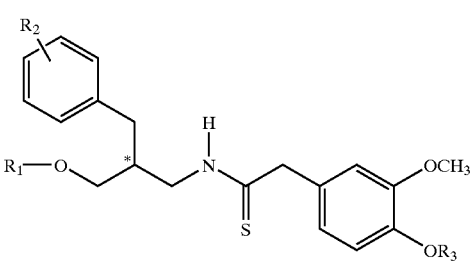

(I-b)

| | $R_1$ | $R_2$ | $R_3$ | $^{45}$Ca Influx (EC$_{50}$ = μM) | Writhing Test (ED$_{50}$ = μG/KG) |
|---|---|---|---|---|---|
| I-a | | | | | |
| 19a | COC(CH$_3$)$_3$ | 3,4-(CH$_3$)$_2$ | CH$_2$CO$_2$H | 7.77 ± 0.80 | 431 |
| 19b | COC(CH$_3$)$_3$ | 4-C(CH$_3$)$_3$ | CH$_2$CO$_2$H | 12.3 ± 1.58 | 365 |
| 23a | COC(CH$_3$)$_3$ | 3,4-(CH$_3$)$_2$ | COCH$_2$CH$_2$CO$_2$H | 7.04 ± 1.3 | 53.1 |
| 23b | COC(CH$_3$)$_3$ | 4-C(CH$_3$)$_3$ | COCH$_2$CH$_2$CO$_2$H | 7.00 ± 1.2 | 60 |
| 36a | COC(CH$_3$)$_3$ | 3,4-(CH$_3$)$_2$ | CH$_2$CH$_2$NH$_2$ | 0.083 ± 0.012 | 14.0 |
| 36b | COC(CH$_3$)$_3$ | 4-C(CH$_3$)$_3$ | CH$_2$CH$_2$NH$_2$ | 0.377 ± 0.067 | 48.2 |
| I-b | | | | | |
| 28a | COC(CH$_3$)$_3$ | 3,4-(CH$_3$)$_2$ | CH$_2$CH$_2$NH$_2$ | 1.57 ± 0.23 | 0.960 |
| 28b | COC(CH$_3$)$_3$ | 4-C(CH$_3$)$_3$ | CH$_2$CH$_2$NH$_2$ | 0.878 ± 0.17 | 8.12 |
| Olvanil | | | | | 17.4 |
| DA-5018 | | | | 0.234 | 2.27 |
| Capsaicin | | | | 0.435 | |

Experimental Example 3

Pungency and Tachyphylaxis

The focus of medicinal chemistry in developing vanilloid-derived therapeutics has been the improvement of the bioavailability and the reduction of the excitatory properties. In connection with these objectives, the rat eye-wiping test was employed as an in vivo pungency test to assess the pain-producing effects of the compounds. As shown in Table 4, pungency profiles of selected potent agonists, 7a-V, 7b-I and 7d-I, didn't follow the trend of the intrinsic agonistic activity measured by two in vitro assays. In this assay, RTX, an ultrapotent capsaicin analogue, was only 3-fold more potent than CAP and the selected compounds from our series were much less potent in evoking acute pain. A possible explanation for the reduced excitatory properties of these synthetic compounds (7b-I and 7d-I) could to lie in their rate of excitation of the sensory neuron.

To check for the development of tachyphylaxis or cross-tachyphylaxis, a group of rats treated with the selected synthetic compounds were challenged 6 h postreatment with 0.001% CAP. CAP, RTX and the synthetic analogues displayed an attenuated eye-wiping response in the test challenge equivalent to 0.001% of CAP, a result that is indicative of cross-tachyphylaxis between these classes of compounds. However, it should be noted that for CAP analogues a prior eye-wiping response is a prerequisite for the development of after-desensitization. In other words, non-irritating doses of CAP analogues were without effect to protect the eye-wiping movement by test treatment with 0.001% CAP.

Methods

Pungency and Tachyphylaxis in the Rat Eye-wiping Test

The pain-inducing potency of the compounds was determined in the eye-wiping assay as previously described, and expressed quantitatively as follows. Solutions in tenfold increasing concentrations in physiological saline, containing at most 5% ethanol, were dropped into the eye of rats weighing 150–180 g, and the number of protective movement (eye-wiping with the foreleg) was counted. Each concentration was applied to 6 rats and the dose-response curves were obtained from the mean values. From the dose-response curves the concentrations having a moderate pain-producing potency (MPP), i.e. inducing an equal response of 10 scratchings, were calculated for each compound. On the basis of these concentrations the relative pain-producing potency (RPP) was determined as compared to that of capsaicin, which was taken as 100. To check for the development of tachyphylaxis or cross-tachyphylaxis, 6 hours following the application of the test compound, a 0.001% test challenge of capsaicin was applied to the same eye. The % reduction of response to a concentration of 0.001% capsaicin in treated rats with the test compounds, compared to the vehicle-treated rats, was estimated to be the index of desensitization.

Results

TABLE 4

Eye-Wiping Test

|  | MPP (%)[a] | RPP[b] | % Reduction |
|---|---|---|---|
| Capsaicin | 0.0003 | 100 | 55 (0.1) |
|  |  |  | 35 (0.01) |
| RTX | 0.0001 | 300 | 85 (0.01) |
|  |  |  | 20 (0.001) |
| Olvanil | WP[c] | — | 0.1 |
| DA-5018 | 0.003 | 10 | 90 (0.1) |
|  |  |  | 35 (0.01) |
| 7a-V | WP | — | 0 (0.1) |
| 7b-I | 0.002 | 15 | 90 (0.1) |
|  |  |  | 30 (0.01) |
|  |  |  | 5 (0.001) |
| 7d-I | 0.003 | 10 | 0 (0.1) |

[a]MPP: moderate pain-producing potency
[b]RPP: relative pain-producing potency
[c]WP: weakly pungent (less pungent than 0.001% capsaicin at 0.01% concentration)

The invention being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A compound represented by the following formula (I):

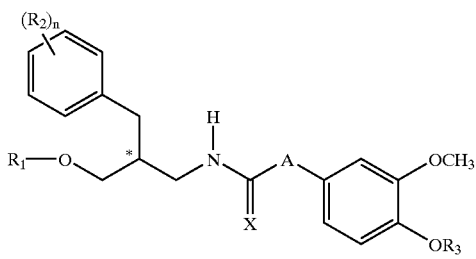

(I)

wherein,
X is an oxygen or sulfur atom;
A is —$NHCH_2$— or —$CH_2$—;
$R_1$ is a substituted or unsubstituted $C_{1-4}$alkaryl group, or the group of the formula: $R_4CO$— wherein $R_4$ is an alkyl group having 1 to 18 carbon atoms, an alkenyl group having 2 to 18 carbon atoms, or a substituted or unsubstituted aryl group having 6 to 10 carbon atoms;
$R_2$ is a hydrogen atom, an alkyl group having 1 to 6 carbon atoms, an alkoxy group having 1 to 6 carbon atoms, a haloalkyl group having 1 to 6 carbon atoms or a halogen atom;
$R_3$ is a hydrogen atom, an alkyl grouip having 1 to 4 carbon atoms, an aminoalkyl, a diacid monoester, α-alkyl acid;
n is an integer of 1 to 2; and
the asterisk mark * indicates a chiral carbon atom, and its pharmaceutically acceptable salts.

2. A compound of claim 1, wherein
$R_1$ is benzyl group or the group of formula: $R_4CO$— wherein $R_4$ is an alkyl group having 1 to 18 carbon atoms, phenyl group, or phenyl group substituted with one or more $C_{1-4}$alkyl groups;
$R_2$ is a hydrogen atom, an alkyl group having 1 to 4 carbon atoms, an alkoxy group having 1 to 4 carbon atoms, a haloalkyl group having 1 to 4 carbon atoms or a halogen atom; and
$R_3$ is a hydrogen atom, an alkyl group having having 1 to 4 carbon atoms, —$(CH_2)_nNH_2$—, —$CO(CH_2)_nCO_2H$ or —$(CH_2)_nCO_2H$ (wherein, n is 1 or 2).

3. A compound of claim 1, wherein X is oxygen atom and A is —$CH_2$—.

4. A compound of claim 1, wherein X is sulfur atom and A is —$NHCH_2$—.

5. A compound of claim 1, wherein $R_3$ is a hydrogen atom, methyoxymethyl group, —$CH_2CH_2NH_2$, —$COCH_2CH_2CO_2H$ or —$CH_2CO_2H$.

6. A compound of claim 1, wherein $R_2$ is selected from the group of consisting of a hydrogen atom, t-butyl, 3,4-(dimethyl) and chloro atom.

7. A compound of claim 1, wherein $R_4$ is selected from the group of consisting of t-butyl, i-propyl, pentyl, heptadecyl, phenyl and 3,4-(dimethyl)phenyl group.

8. A compound of claim 1, which is one selected from the group of consisting of
2,2-dimethyl propionic acid 2-({2-[4-(2-aminoethoxy)-3-methoxyphenyl]acetylamino}methyl)-3-(3,4-dimethylphenyl)propyl ester;
2,2-dimethyl propionic acid 2-({2-[4-(2-aminoethoxy)-3-methoxyphenyl]acetylamino}methyl)-3-(4-tert-butylphenyl)propyl ester;
2,2-dimethyl propionic acid 2-benzyl 3-[3-(4-hydroxy-3-methoxybenzyl)thioureido]propyl ester;
2-methyl propionic acid 2-benzyl 3-[3-(4-hydroxy-3-methoxybenzyl)thioureido]propyl ester;
2,2-dimethyl propionic acid 2-(3,4-dimethylbenzyl)-3-[3-(4-hydroxy-3-methoxybenzyl)thioureido]propyl ester; and
2,2-dimethyl propionic acid 2-(4-tert-butylbenzyl)-3-[3-(4-hydroxy-3-methoxybenzyl)thioureido]propyl ester.

9. A pharmaceutical composition comprising the compound (I) as an active ingredient together with a pharmaceutically acceptable carrier.

10. A pharmaceutical composition of claim 9, which comprises the compound (I) as an active ingredient in an amount effective to alleviate or relieve acute, chronic, inflammatory or neuropathic pains, suppress inflammation, or treat urge incontinence together with a pharmaceutically acceptable carrier.

11. A method of alleviating or relieving acute, chronic, inflammatory or neuropathic pains of suppressing inflammation or treating urge incontinence which comprises administering to a subject suffering from such pains, inflammation or incontinence the compound (I) in an amount effective for alleviating or releiving the pains, inflammation or incontinence.

12. A method of treating bladder hypersensitivity which comprises administering to a subject requiring such treatment the compound (I) in an amount effective for alleviating or relieving the bladder hypersensitivity.

* * * * *